US010968278B2

(12) United States Patent
Sridhara Sundaram et al.

(10) Patent No.: US 10,968,278 B2
(45) Date of Patent: Apr. 6, 2021

(54) COMPOSITIONS COMPRISING IL6R ANTIBODIES FOR THE TREATMENT OF UVEITIS AND MACULAR EDEMA AND METHODS OF USING SAME

(71) Applicants: SANOFI BIOTECHNOLOGY, Paris (FR); REGENERON PHARMACEUTICALS, INC., Tarrytown, NY (US)

(72) Inventors: Preethi Aavali Sridhara Sundaram, Belle Mead, NJ (US); Ronald Buggage, Paris (FR); Karen W. Chu, White Plains, NY (US); Valérie Corp dit Genti, Buisson (FR); Kristine A. Erickson, Roxbury, CT (US); Dominique Mery-Mignard, Montgeron (FR); Rafael Varona, Paris (FR); Robert L. Vitti, Old Tappan, NJ (US)

(73) Assignees: SANOFI BIOTECHNOLOGY, Paris (FR); REGENERON PHARMACEUTICALS, INC., Tarrytown, NY (US)

( * ) Notice: Subject to any disclaimer, the term of this patent is extended or adjusted under 35 U.S.C. 154(b) by 346 days.

(21) Appl. No.: 15/342,833

(22) Filed: Nov. 3, 2016

(65) Prior Publication Data

US 2017/0166646 A1 Jun. 15, 2017

Related U.S. Application Data

(60) Provisional application No. 62/408,391, filed on Oct. 14, 2016, provisional application No. 62/250,269, filed on Nov. 3, 2015.

(30) Foreign Application Priority Data

Sep. 14, 2016 (EP) .................................... 16306166

(51) Int. Cl.
| | |
|---|---|
| *C07K 16/28* | (2006.01) |
| *A61K 39/395* | (2006.01) |
| *A61K 39/00* | (2006.01) |
| *A61K 31/519* | (2006.01) |
| *A61K 31/573* | (2006.01) |

(52) U.S. Cl.
CPC ........ *C07K 16/2866* (2013.01); *A61K 31/519* (2013.01); *A61K 31/573* (2013.01); *A61K 39/395* (2013.01); *A61K 39/3955* (2013.01); *A61K 2039/505* (2013.01); *A61K 2039/54* (2013.01); *A61K 2039/545* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,046,223 A | 4/2000 | Sponsel et al. | |
| 6,629,949 B1 | 10/2003 | Douglas | |
| 6,659,982 B2 | 12/2003 | Douglas et al. | |
| 8,080,248 B2* | 12/2011 | Radin ................ | A61K 31/4706 424/130.1 |
| 8,895,521 B2 | 11/2014 | Klinman et al. | |
| 9,139,646 B2 | 9/2015 | Solinger et al. | |
| 2009/0082288 A1 | 3/2009 | Klinman et al. | |
| 2013/0149310 A1 | 6/2013 | Jasson et al. | |
| 2014/0302053 A1 | 10/2014 | Huang et al. | |
| 2015/0050277 A1 | 2/2015 | Peters et al. | |
| 2016/0280782 A1 | 9/2016 | Huang et al. | |

FOREIGN PATENT DOCUMENTS

| | | |
|---|---|---|
| EP | 0 628 639 A1 | 12/1994 |
| EP | 0 783 893 A1 | 7/1997 |
| WO | 1992/019759 A1 | 11/1992 |
| WO | 1996/011020 A1 | 4/1996 |
| WO | 2013/053751 A1 | 4/2013 |
| WO | WO 2015/148790 A1 | 1/2015 |
| WO | 2015/077582 A1 | 5/2015 |
| WO | WO 2017/079443 A1 | 5/2017 |

OTHER PUBLICATIONS

Phase II Study to analyze Sarilumab in Non-Infectious Uveitis NCT01900431 (Year: 2014).*
Lin, P., Clinical Ophthalmology., vol. 9, pp. 1697-1702. (Year: 2015).*
Adan et al. (Jul. 27, 2013) "Tocilizumab treatment for refractory uveitis-related cystoid macular edema," Graefe's Archive for Clinical and Experimental Ophthalmology. 251(11):2627-2632; DOI 10.1007/s00417-013-2436-y.
Anonymous (Oct. 29, 2012) "NCT01717170 : Study of the Safety, Tolerability, and Bioactivity of Tocilizumab on Patients With Non-infectious UVEITIS: The STOP-UVEITIS Study," ClinicalTrials.gov Archive. Retrieved from the Internet: https://clinicaltrials.gov/archive/NCT01717170/2012_10_29 [Last Accessed Apr. 5, 2017]].
Anonymous (Apr. 13, 2015) "NCT01900431: Phase II Study to Analyze Sarilumab in Non-Infectious Uveitis," ClinicalTrials.gov Archive. Retrieved from the Internet: https://clinicaltrials.gov/archive/NCT01900431/2015_04_13 [Last Accessed Apr. 5, 2017]].

(Continued)

*Primary Examiner* — Gary B Nickol
*Assistant Examiner* — Jegatheesan Seharaseyon
(74) *Attorney, Agent, or Firm* — Lathrop GPM LLP; James H. Velema; Judith L. Stone-Hulslander

(57) ABSTRACT

The present invention provides compositions and methods of treating and improving the symptoms of uveitis and/or macular edema using an antibody that specifically binds human interleukin-6 receptor (hIL-6R).

24 Claims, No Drawings

Specification includes a Sequence Listing.

(56) References Cited

OTHER PUBLICATIONS

Arevalo (Nov. 25, 2014) "Tocilizumab shows promise for refractory uveitis-related macular edema," American Academy of Ophthalmology. Accessible on the Internet at URL: https://www.aao.org/editors-choice/tocilizumab-shows-promise-refractory-uveitisrelate. [Last Accessed Apr. 10, 2017].
Barry et al. (Sep. 22, 2014) "Pharmacotherapy for uveitis: current management and emerging therapy," Clinical Ophthalmology. 8:1891-1911.
Kawashima et al. (Apr. 6, 2007) "Soluble IL-6 Receptor in Vitreous Fluid of Patients with Proliferative Diabetic Retinopathy," Japanese Journal of Ophthalmology. 51(2):100-104.
Lin (Sep. 11, 2015) "Targeting interleukin-6 for noninfectious uveitis," Clinical Ophthalmology. 9:1697-1702.
Merida et al. (Aug. 11, 2015) "New Immunosuppressive Therapies in Uveitis Treatment," International Journal of Molecular Sciences, 16(8):18778-18795.
Mesquida et al. (Dec. 1, 2014) "Long-Term Effects of Tocilizumab Therapy for Refractory Uveitis-Related Macular Edema," Ophthalmology. 121(12):2380-2386; DOI: http://dx.doi.org/10.1016/j.ophtha.2014.06.050.
Nguyen et al. (Jul. 1, 2015) "The Saturn Study (SARIL-NIU): Sarilumab for the Treatment of Posterior Segment Non-Infectious Uveitis (NIU)," Invest. Ophthalmol. Vis. Sci. 56(7):3116; ARVO Annual Meeting Abstract.
Rafique et al. (Jun. 23, 2013) "AB3007 Evaluation of the binding kinetics and functional bioassay activity of sarilumab and tocilizumab to the human il-6 receptor (il-6r) alpha," Annals of the Rheumatic Diseases. 72(Supplement 3):A797.
Bresnick (1986) "Diabetic macular edema. A review," Ophthalmology. 93(7):989-997.
Cao et al. (Jun. 2013) "Pharmacological blockade of interleukin 6 receptor (IL-6R) inhibits the development of ocular inflammation in the murine model of experimental autoimmune uveitis (EAU)," Investigative Ophthalmology & Visual Science. 54:5193.
Davis et al. (2010) "Scale for photographic grading of vitreous haze in uveitis," Am. J. Ophthalmol. 150(5): 637-641.
Durrani et al. (2004) "Degree, duration, and causes of visual loss in uveitis," Br. J. Ophthalmol. 88(9):1159-1162.
Gordon et al. (1998) "pANCA antibodies in patients with anterior uveitis: identification of a marker antibody usually associated with ulcerative colitis," J. Clin. Immunol. 18(4):264-271.
Hirata et al. (1989) "Characterization of IL-6 receptor expression by monoclonal and polyclonal antibodies," J. Immunol. 143:2900-2906.
Kishimoto (2003) "Interleukin-6 (IL-6)," Ch. 12 In; The Cytokine Handbook. Ed: Thomson. Academic Press. London, United Kingdom. pp. 281-304.
Langer (1990) "New methods of drug delivery," Science. 249:1527-1533.
Lipsky (2006) "Interleukin-6 and rheumatic diseases," Arthritis Res. Ther. 8(Suppl 2):S4. pp. 1-5.
Meehan et al. (1996) "A microinfusor device for the delivery of therapeutic levels of peptides and macromolecules," J. Controlled Release 46:107-116.
Nussenblatt et al. (1985) "Standardization of Vitreal inflammatory Activity in Intermediate and Posterior Uveitis," Ophthalmology. 92(4):467-471.
Ongkosuwito et al. (1998) "Analysis of Immunoregulatory Cytokines in Ocular Fluid Samples From Patients With Uveitis," Invest Ophthalmol Vis Sci. 39(13):2659-2665.
Perez et al. (2004) "Elevated levels of interleukin 6 in the vitreous fluid of patients with pars planitis and posterior uveitis: the Massachusetts eye & ear experience and review of previous studies," Ocul. Immunol. Inflamm. 12 (3):193-201.
Powell et al. (1998) "Compendium of excipients for parenteral formulations," PDA J. Pharm. Sci. Technol. 52:238-311.
Rose-John et al. (2006) "Interleukin-6 biology is coordinated by membrane-bound and soluble receptors: role in inflammation and cancer," J. Leukoc. Biol. 80(2):227-236.
Suttorp-Schulten et al. (1996) "Recent developments in the treatment of posterior uveitis," Ocul. Immunol. Inflamm. 4(4):207-217.
Valentincic et al. (2011) "Intraocular and serum cytokine profiles in patients with intermediate uveitis," Mol. Vis. 17:2003-2010.
Wu et al. (1987) "Receptor-mediated in vitro gene transformation by a soluble DNA carrier system," J. Biol. Chem. 262:4429-4432.
Yoshimura et al. (2009) "Comprehensive Analysis of Inflammatory Immune Mediators in Vitreoretinal Diseases," PloS One. 4(12):e8158. pp. 1-9.
PCT/EP2012/070052 / 2013/053751, Oct. 10, 2012 / Apr. 18, 2013, Xiaohong Huang.
PCT/US2014/066856 / 2015/077582, Nov. 21, 2014 / May 28, 2015, Xiaohong Huang.
"International Search Report and Written Opinion received for PCT Patent Application No. PCT/US2016/060344, dated Mar. 13, 2017", 13 pages.
Riancho-Zarrabeitia, et al., "Efficacy of Tocilizumab in Patients with Uveitis Refractory to Other Biologic Drugs: A Multicenter Study on 31 Cases", 2014 ACR/ARHP Annual Meeting Abstract Number: 1249, Retrieved from: «https://acrabstracts.org/abstract/efficacy-of-Tocilizumab-in-patients-with-uveitis-refractory-to-other-biologic-drugs-a-multicenter-study-on-31-cases/».
Fortin et al., "Glossary of Selected Terms — A Systematic Review of Intravitreal Bevacizumab for the Treatment of Diabetic Macular Edema", NCBI Bookshelf, May 1, 2012, pp. 1-2, retrieved from url: https://www.ncbi.nlm.nih.gov/books/NBK169468/.

* cited by examiner

SEQUENCE LISTING

```
<160> NUMBER OF SEQ ID NOS: 5

<210> SEQ ID NO 1
<211> LENGTH: 358
<212> TYPE: PRT
<213> ORGANISM: Homo sapiens

<400> SEQUENCE: 1

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140
```

```
Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
            165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
            245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
            325                 330                 335

Asn Lys Asp Asp Asp Asn Ile Leu Phe Arg Asp Ser Ala Asn Ala Thr
            340                 345                 350

Ser Leu Pro Val Gln Asp
        355

<210> SEQ ID NO 2
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
            85                  90                  95

Ala Lys Gly Arg Asp Ser Phe Asp Ile Trp Gly Gln Gly Thr Met Val
            100                 105                 110

Thr Val Ser Ser
        115
```

-continued

```
<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 4
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

-continued

```
                195                 200                 205
Lys Val Asp Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys
            435                 440                 445
```

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 5

```
Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Gly Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Ser Tyr Tyr Cys Gln Gln Ala Asn Ser Phe Pro Tyr
                85                  90                  95
Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

COMPOSITIONS COMPRISING IL6R ANTIBODIES FOR THE TREATMENT OF UVEITIS AND MACULAR EDEMA AND METHODS OF USING SAME

RELATED APPLICATIONS

This application claims priority to U.S. provisional application Ser. No. 62/408,391, filed Oct. 14, 2016; European patent application number EP16306166.6, filed Sep. 14, 2016; and U.S. provisional application Ser. No. 62/250,269, filed Nov. 3, 2015, each of which is incorporated by reference herein in its entirety.

FIELD OF THE INVENTION

The present invention relates to the field of therapeutic treatment of uveitis and/or macular edema. More specifically, the invention relates to the use of interleukin-6 receptor (IL-6R) antagonists, such as anti-IL-6R antibodies to treat uveitis.

BACKGROUND

Interleukin-6 is a key cytokine with a wide range of biological activities, including regulation of immune reactivity, the acute-phase response, inflammation, oncogenesis and hematopoiesis (Kishimoto T., The Cytokine Handbook, A. W. Thomson, Lotze, M. T., ed. (London: Academic Press). 2003 pp. 281-304). Overproduction of IL-6 has been found to play pathological roles in chronic inflammatory diseases, including rheumatoid arthritis (RA). IL-6 has been also consistently shown to be elevated in the vitreous of patients with non-infectious uveitis (Ongkosuwito et al., Invest Ophthalmol Vis Sci. 1998; 39(13):2659-65; Perez et al., Ocul Immunol Inflamm. 2004; 12(3):193-201; Yoshimura et al., PloS One. 2009; 4(12):e8158; and Valentincic et al., Mol Vis. 2011; 17:2003-10. Epub 2011 Jul. 20).

IL-6 interacts directly with the IL-6Ra subunit and the IL-6/IL-6Ra pair forms a high affinity complex with the glycoprotein 130 (gp130) subunit. IL-6Ra also exists in a soluble form, which is involved in trans-signaling and allows IL-6 to affect cells that do not express IL-6Ra including synovial cells in the joint (Rose-John et al., J Leukoc Biol. 2006; 80(2), 227-36).

Sarilumab (SAR153191), also designated as REGN88, is co-developed by Sanofi and Regeneron. Sarilumab is a recombinant IgG1 kappa monoclonal antibody of fully human sequence directed against the alpha subunit of the IL-6 receptor complex (IL-6Rα). Sarilumab is a potent and specific inhibitor of IL-6 signaling. By binding to IL-6Rα with high affinity, sarilumab blocks the binding of IL-6 and interrupts the cytokine-mediated signaling cascade. Sarilumab is being evaluated in Phase 3 clinical trials for the treatment of RA. In addition, a proof of concept study is now ongoing for the treatment of patients with non-infectious, intermediate, posterior or pan-uveitis. Interleukin-6 is a key element in the etiology of rheumatic conditions and inhibition of its signaling is a critical part of the mechanism of action of sarilumab.

Proinflammatory cytokines associated with RA include tumor necrosis factor alpha (TNF-α), interleukin-1 (IL-1), and IL-6. Interleukin-6 is expressed in a large proportion of cells in rheumatoid synovium and elevated levels of IL-6 are found in the serum and synovial fluid of patients with RA. Elevated levels of soluble IL-6R α have also been observed in a variety of inflammatory diseases, including RA (Lipsky P E. Interleukin-6 and rheumatic diseases. Arthritis Res Ther. 2006; 8 (Suppl 2): S4). Interaction of IL-6 with soluble IL-6R a results in formation of soluble complexes that are able to transactivate gp130 present on a number of cell surfaces, potentially a major pathogenic mechanism in RA (Rose-John et al., J Leukoc Biol. 2006; 80(2), 227-36). IL-6 is downstream from TNF-α and IL-1 in inflammatory cytokine cascades and may therefore represent a final common signaling pathway in a wide range of inflammatory processes. Rheumatoid arthritis is a chronic inflammatory disease characterized by persistent synovitis and progressive destruction of cartilage and bone in multiple joints. Associated systemic inflammatory symptoms include fever, fatigue, anemia, increased acute phase reactants such as erythrocyte sedimentation rate (ESR) and C-reactive protein (CRP), and the development of auto-antibodies such as rheumatoid factor (RF) (Kishimoto T., The Cytokine Handbook, A. W. Thomson, Lotze, M. T., ed. (London: Academic Press). 2003 pp. 281-304).

Uveitis is a term used to describe a group of intraocular inflammatory diseases that can occur at any age, but predominantly affects patients in the working age group (Nussenblatt et al., Ophthalmology 1985; 92(4):467-471). Non-infectious uveitis (NIU) may result from an underlying inflammatory disease, an autoimmune disorder, a tumor or as a result of trauma to the eye. In most cases, the cause remains unknown (ie, idiopathic uveitis) (Durrani et al., Br J Ophthalmol. 2004; 88(9):1159-62).

The goal in the treatment of NIU is to control inflammation, prevent loss of vision, and minimize long term complications of the disease and its treatment. Systemic corticosteroids are widely used for the management of posterior segment inflammation which requires treatment, particularly when it is associated with systemic disease or when bilateral ocular disease is present. As IL-6 has been consistently shown to be elevated in the vitreous of patients with NIU (Ongkosuwito et al. Invest Ophthalmol Vis Sci. 1998; 39(13):2659-65; Perez et al. Ocul Immunol Inflamm. 2004; 12(3):193-201; Yoshimura et al., PloS One. 2009; 4(12): e8158; Valentincic et al. Mol Vis. 2011; 17:2003-10. Epub 2011 Jul. 20), blockade of IL-6 signaling throughIL-6Ra with sarilumab may have potential as a treatment in this disease.

To support the treatment of non-infectious uveitis following subcutaneous injection of sarilumab to patients, the efficacy of the murine surrogate antibody against IL-6Rα (REGN844), was investigated in a murine organ-specific T lymphocyte-mediated model of experimental autoimmune uveoretinitis (EAU). In the study, REGN844 given intraperitoneally (IP) to mice at dose-levels from 10 to 100 mg/kg every third day from Day 5 post-EAU induction, resulted in a dose-related inhibition of non-infectious uveitis as evidenced by reductions in retinal thickness, morphological abnormalities and inflammatory cell infiltration, confirmed by both histological and optical coherence tomography (OCT) measurements. Systemic (intraperitoneal) administration of a mouse anti-murine IL6R antibody (REGN844) consistently ameliorates the development of vitreoretinal inflammation in the mouse model of experimental autoimmune uveitis (EAU) (Cao, J, et. al: Investigative Ophthalmology & Visual Science June 2013, Vol. 54, 5193).

Macular edema involves the abnormal leakage and accumulation of fluid in the macula from damaged blood vessels in the nearby retina. A common cause of macular edema is diabetic retinopathy. See Bresnick 1986 Ophthalmology, 93(7): pages 989-97. Macular edema can also occur after eye surgery, in association with age-related macular degeneration, or as a consequence of inflammatory diseases that affect the eye. In fact, any disease that damages blood vessels in the retina can cause macular edema.

Sarilumab (SAR153191), also known as REGN88, is being evaluated for the treatment of rheumatoid arthritis (RA) and for the treatment of non-infectious intermediate, posterior and pan-uveitis. Sarilumab is a recombinant human monoclonal antibody of the immunoglobulin G1 (IgG1) kappa isotype directed against the interleukin-6 receptor a-subunit (IL-6Ra). Sarilumab binds the human IL-6Ra and has been demonstrated to block interleukin-6 (IL-6) signaling and to not induce signaling in the absence of IL-6. In ex vivo assays, sarilumab did not demonstrate antibody-dependent cellular cytotoxicity (ADCC) or complement-dependent cytotoxicity (CDC) on relevant cell types where sarilumab binding was verified by fluorescence-activated cell sorter (FACS) analysis.

SUMMARY

An aspect of the invention provides a method for treating macular edema in a subject in need thereof comprising administering an effective amount of an antibody that specifically binds IL-6 receptor.

In various embodiments, the antibody that specifically binds to the IL-6 receptor comprises a heavy chain variable region of sequence SEQ ID NO:2 and the light chain variable region sequence of SEQ ID NO:3. In various embodiments of the method, the antibody is sarilumab.

In various embodiments of the method, subject is suffering from at least one symptom of macular edema. In various embodiments, the at least one symptom is selected from the group consisting of: ocular inflammation, impaired vision, impaired color recognition, tissue thickening, and leakage of ocular vessels. For example, the subject has blurry vision. In various embodiments of the method, the subject suffering from the at least one symptom of macular edema is improved after administering the antibody.

In various embodiments of the method, the subject is suffering from cystoid macular edema. In various embodiments of the method, the subject is suffering from diabetic retinopathy.

In various embodiments the macular edema is macular edema secondary to uveitis. For example, the uveitis is selected from the group consisting of intermediate uveitis, posterior uveitis and pan-uveitis.

In various embodiments of the method, subject has a central retinal thickness (CRT) greater than 300 μm.

In various embodiments of the method, the subject suffering from at least one symptom of uveitis is improved after administering the antibody. In various embodiments, the is symptom of uveitis is selected from the group consisting of: vitreous haze (VH) level, best corrected visual acuity (BCVA), signs of ocular inflammation, retinal vessel leakage, central retinal thickness, and ocular inflammation in the anterior chamber.

In various embodiments, the subject is suffering from at least one symptom of macular edema and from at least one symptom of uveitis. In various embodiments of the method, the subject suffering from both of these symptoms is improved after administering the antibody.

In various embodiments of the method, the subject has been previously treated for at least three months with a corticosteroid. For example, the corticosteroid is prednisone. In various embodiments, the prednisone was administered from 15 to 80 mg/day.

In various embodiments of the method, the subject was also administered methotrexate. For example, the methotrexate was administered from 6 to 25 mg/week.

In various embodiments of the method, the subject is also administered a corticosteroid. For example, the corticosteroid is prednisone. In various embodiments of the method, the prednisone is administered from 15 to 80 mg/day.

In various embodiments of the method, the subject is also administered methotrexate. For example, the methotrexate is administered from 6 to 25 mg/week.

In various embodiments, the subject achieves after 16 weeks a reduction in the VH level on the Miami 9 point scale of at least 2 steps or a reduction of corticosteroid dose to less than 10 mg per day.

In various embodiments, the subject achieves after 16 weeks a reduction in the VH level on the Miami 9 point scale of at least 2.

In various embodiments, the subject achieves after 16 weeks a reduction of corticosteroid dose to less than 10 mg per day.

In various embodiments, the subject experiences a greater than 20% reduction in CRT, greater than 10 letters of improvement in BCVA, shows a reduction in retinal vessel leakage and/or an improvement in uveitis clinical assessment score. For example, the assessment score is calculated using feedback from the subject and/or is determined using an assessment and/or procedure by a physician. For example, the improvement or reduction is relative to a healthy subject, or to a control value or a sample from the subject having uveitis and/or macular edema prior to having the ocular condition.

In various embodiments, the subject achieves after 16 weeks an improvement in BCVA.

In various embodiments, the subject achieves after 16 weeks an improvement in CRT.

In various embodiments, the subject achieves after 16 weeks an improvement in retinal vessel leakage.

In various embodiments, the subject achieves after 16 weeks an improvement in a clinical assessment score.

In various embodiments of the method, the antibody is administered subcutaneously. In various embodiments, the antibody is administered intravenously.

In various embodiments of the method, the antibody is administered from about 150 to about 200 mg once every two weeks. For example, the antibody is administered subcutaneously.

In various embodiments of the method, the antibody is administered at about 150 mg once every two weeks. In various embodiments of the method, the antibody is administered at about 200 mg once every two weeks.

In various embodiments of the method, the antibody is tocilizumab. For example, the tocilizumab is administered intravenously at from about 4 to about 8 mg/kg once every four weeks. In various embodiments, the tocilizumab is administered subcutaneously at about 162 mg once a week or once every two weeks.

An aspect of the invention provides an antibody for use in a method for treating uveitis and/or macular edema in a subject, wherein the antibody specifically binds IL-6 receptor, optionally wherein the subject has a VH level greater than or equal to 2 on the Miami 9 step scale or wherein the subject has a CRT greater than 300 μm.

In addition, the present disclosure provides a method for treating uveitis in a subject in need thereof comprising administering an effective amount of an antibody that specifically binds IL-6 receptor, wherein the subject has a VH level greater than or equal to 2 on the Miami 9 step scale or wherein the subject has a CRT greater than 300 μm. The subject can have a VH level greater than or equal to 3, 4, 5, 6, 7 or 8 on the Miami 9 step scale. The subject can have a VH level greater than or equal to 4 on the Miami 9 step scale.

The uveitis can in various embodiments be selected from the group consisting of intermediate uveitis, posterior uveitis and pan-uveitis. The uveitis can in various embodiments be non-infectious uveitis. In various embodiments, the uveitis can be systemic or idiopathic. The subject can be suffering from macular edema. The subject can in various embodiments have a CRT greater than 300 μm. The subject can in various embodiments have other signs of intraocular inflammation. In certain specific embodiments, the other signs of intraocular inflammation are selected from the group consisting of perivascular sheathing of retinal vessels and leakage of retinal vessels.

In some embodiments, the subject has been suffering from uveitis for at least three months.

In certain embodiments, at least one symptom of uveitis in the subject is improved. The symptom of uveitis can be selected from the group consisting of VH level, BCVA, macular edema, signs of ocular inflammation, retinal vessel leakage, CRT and ocular inflammation in the anterior chamber. For example, the symptom of uveitis (e.g., VH level) is determined by comparison to a healthy individual without uveitis and/or macular edema, or to a control value or a sample from the subject prior to having uveitis and/or macular edema.

In some specific embodiments, the subject has been treated for at least three months with a corticosteroid. In particular embodiments, the corticosteroid is prednisone. In some embodiments, the prednisone was administered from 15 to 80 mg/day.

In certain specific embodiments, the subject was also administered methotrexate. In some embodiments, the methotrexate was administered from 6 to 25 mg/week.

In some embodiments, the subject is administered a corticosteroid. The corticosteroid can in various embodiments be prednisone. In some specific embodiments, the prednisone was administered from 15 to 80 mg/day.

In some specific embodiments, the subject is also administered methotrexate. In various embodiments, the methotrexate may be administered from 6 to 25 mg/week.

In certain embodiments, the subject achieves after 16 weeks a reduction in the VH level on the Miami 9 point scale of at least 2 steps or a reduction of corticosteroid dose to less than 10 mg per day. In certain specific embodiments, the subject achieves after 16 weeks a reduction in the VH level on the Miami 9 point scale of at least 2. In some embodiments, the subject achieves after 16 weeks a reduction of corticosteroid dose to less than 10 mg per day.

In some specific embodiments, the subject experiences a greater than 20% reduction in CRT, greater than 10 letters of BCVA, shows a reduction in retinal vessel leakage and/or an improvement in uveitis clinical assessment score. In certain embodiments, the subject achieves after 16 weeks an improvement in BCVA. In some embodiments, the subject achieves after 16 weeks an improvement in CRT. In certain specific embodiments, the subject achieves after 16 weeks an improvement in retinal vessel leakage. In some specific embodiments, the subject achieves after 16 weeks an improvement in uveitis clinical assessment score.

In any embodiment, the antibody that specifically binds to the IL-6 receptor can be an antibody that comprises a heavy chain variable region of amino acid sequence SEQ ID NO:2 and the light chain variable region amino acid sequence of SEQ ID NO:3. In some embodiments, the antibody is administered from about 150 mg to about 200 mg once every two weeks. In various embodiments, the antibody is administered at about 150 mg once every two weeks. In various embodiments, the antibody is administered at about 200 mg once every two weeks. In some specific embodiments, the antibody is sarilumab.

In certain embodiments, the antibody is tocilizumab. In certain specific embodiments, the tocilizumab is administered intravenously at from about 4 to about 8 mg/kg once every four weeks. In various embodiments, the tocilizumab is administered subcutaneously at about 162 mg once a week or once every two weeks.

An aspect of the invention provides an antibody for use in a method of treating uveitis and/or macular edema in a subject, wherein the antibody comprises a heavy chain variable region of sequence SEQ ID NO:2 and the light chain variable region sequence of SEQ ID NO:3.

In addition, the present disclosure also provides a method of treating uveitis in a subject in need thereof comprising administering to the subject a therapeutically effective amount of an antibody, wherein the antibody comprises a heavy chain variable region of sequence SEQ ID NO:2 and the light chain variable region sequence of SEQ ID NO:3. In some embodiments, the antibody is sarilumab.

The uveitis can in various embodiments be selected from the group consisting of intermediate uveitis, posterior uveitis and pan-uveitis. The uveitis can in various embodiments be non-infectious uveitis. The uveitis can be systemic or idiopathic.

In some specific embodiments, the subject has a VH level greater than or equal to 2 on the Miami 9 step scale. In certain specific embodiments, the subject has a VH level greater than or equal to 3, 4, 5, 6, 7 or 8 on the Miami 9 step scale. In some embodiments, the subject has a VH level greater than or equal to 4 on the Miami 9 step scale.

In certain embodiments, the subject is suffering from macular edema. In certain specific embodiments, the subject has a CRT greater than 300 μm. In some embodiments, the subject has other signs of intraocular inflammation. In some embodiments, the other signs of intraocular inflammation are selected from the group consisting of perivascular sheathing of retinal vessels and leakage of retinal vessels. In some specific embodiments, the subject has been suffering from uveitis for at least three months.

In some embodiments, at least one symptom of uveitis in the subject is improved. The symptom of uveitis can in various embodiments be selected from the group consisting of VH level, BCVA, macular edema, signs of ocular inflammation, CRT and ocular inflammation in the anterior chamber.

In certain embodiments, the subject has been treated for at least three months with a corticosteroid. For example, the corticosteroid can be prednisone. In some embodiments, the prednisone was administered from 15 to 80 mg/day. In some specific embodiments, the subject was also administered methotrexate. In particular embodiments, the methotrexate was administered from 6 to 25 mg/week.

In some embodiments, the subject is administered a corticosteroid. The corticosteroid can be prednisone. In some specific embodiments, the prednisone was administered from 15 to 80 mg/day.

In some specific embodiments, the subject is also administered methotrexate. In certain embodiments, the methotrexate is administered from 6 to 25 mg/week.

In certain embodiments, the subject achieves after 16 weeks a reduction in the VH level on the Miami 9 point scale of at least 2 steps or a reduction of corticosteroid dose to less than 10 mg per day. In certain specific embodiments, the subject achieves after 16 weeks a reduction in VH level on the Miami 9 point scale of at least 2. In some embodiments, the subject achieves after 16 weeks a reduction of corticosteroid dose to less than 10 mg per day. In some specific embodiments, the subject experiences a greater than 20% reduction in CRT, greater than 10 letters of BCVA, shows a reduction in retinal vessel leakage and/or an improvement in uveitis clinical assessment score. In certain embodiments, the subject achieves after 16 weeks an improvement in BCVA. In certain specific embodiments, the subject achieves after 16 weeks an improvement in CRT. In some embodiments, the subject achieves after 16 weeks an improvement in retinal vessel leakage. In some specific embodiments, the subject achieves after 16 weeks an improvement in uveitis clinical assessment score.

An aspect of the invention provides a composition for use in the treatment of macular edema in a subject in need thereof, the composition comprising an effective amount of an antibody that specifically binds IL-6 receptor.

In various embodiments, the antibody that specifically binds to the IL-6 receptor comprises a heavy chain variable region of sequence SEQ ID NO: 2 and the light chain variable region sequence of SEQ ID NO: 3. For example, the antibody is sarilumab.

In various embodiments, the subject is suffering from at least one symptom of macular edema selected from the group consisting of: ocular inflammation, impaired vision, impaired color recognition, tissue thickening, and leakage of ocular vessels. For example the macular edema is cystoid macular edema. In various embodiments, the subject is suffering from diabetic retinopathy. In various embodiments, the macular edema is secondary to uveitis. For example, the uveitis is selected from the group consisting of intermediate uveitis, posterior uveitis and pan-uveitis (or panuveitis).

In various embodiments, the subject has a CRT greater than 300 μm.

In various embodiments, the at least one symptom of macular edema in the subject is improved after administering the antibody.

In various embodiments, at least one symptom of uveitis in the subject is improved after administering the antibody. In various embodiments, the symptom of uveitis is selected from the group consisting of: VH level, BCVA, signs of ocular inflammation, retinal vessel leakage, central retinal thickness, and ocular inflammation in the anterior chamber.

In various embodiments, the subject has been previously treated for a period of time with corticosteroids. For example, the period is at least one month, two months or three months with a corticosteroid. In various embodiments, the corticosteroid is prednisone. For example, the prednisone was administered from 15 to 80 mg/day.

In various embodiments, the subject was also administered methotrexate. For example, the methotrexate was administered from 6 to 25 mg/week.

In various embodiments, the subject is also administered a corticosteroid. For example, the corticosteroid is prednisone. In various embodiments, the prednisone was administered from 15 to 80 mg/day.

In various embodiments, the subject is also administered methotrexate. For example, the methotrexate is administered from 6 to 25 mg/week.

In various embodiments, the subject achieves after 16 weeks a reduction in the VH level on the Miami 9 point scale of at least 2 steps or a reduction of corticosteroid dose to less than 10 mg per day. In various embodiments, the subject achieves after 16 weeks a reduction in the VH level on the Miami 9 point scale of at least 2. In various embodiments, the subject achieves after 16 weeks a reduction of corticosteroid dose to less than 10 mg per day. In various embodiments, the subject experiences a greater than 20% reduction in CRT, greater than 10 letters of BCVA, shows a reduction in retinal vessel leakage and/or an improvement in uveitis clinical assessment score.

In various embodiments, the subject achieves after 16 weeks an improvement in BCVA. In various embodiments, the subject achieves after 16 weeks an improvement in CRT. In various embodiments, the subject achieves after 16 weeks an improvement in retinal vessel leakage. In various embodiments, the subject achieves after 16 weeks an improvement in a clinical assessment score.

In various embodiments, the antibody comprises is administered subcutaneously. In various embodiments, the antibody is administered from about 150 to about 200 mg once every two weeks. In various embodiments, the antibody is administered at about 150 mg once every two weeks.

In various embodiments, the antibody is tocilizumab. For example, the tocilizumab is administered intravenously at from about 4 to about 8 mg/kg once every four weeks. In various embodiments, the tocilizumab is administered subcutaneously at about 162 mg once a week or once every two weeks.

An aspect of the invention provides a composition for use in the treatment of uveitis, wherein the composition comprises an effective amount of an antibody that specifically binds IL-6 receptor. In various embodiments, the subject has a VH level greater than or equal to 2 on the Miami 9 step scale or wherein the subject has a CRT greater than 300 μm. For example, the subject has a VH level greater than or equal to 3, 4, 5, 6, 7, or 8 on the Miami 9 step scale. In various embodiments, the subject has a VH level greater than or equal to 4 on the Miami 9 step scale.

In various embodiments of the use, the uveitis is selected from the group consisting of intermediate uveitis, posterior uveitis and pan-uveitis. In various embodiments, the uveitis is non-infectious uveitis. In various embodiments, the uveitis is systemic or idiopathic.

The subject in various embodiments is suffering from macular edema.

In various embodiments, the subject has a CRT greater than 300 μm. For example, the CRT is about 350 μm, 400 μm, 450 μm, 500 μm, 550 μm, 600 μm, 650 μm, 700 μm, 750 μm, 800 μm, or greater than 800 μm.

In various embodiments of the use, the subject has another sign or another symptom intraocular inflammation. For example, the other signs of intraocular inflammation are selected from the group consisting of perivascular sheathing of retinal vessels and leakage of retinal vessels.

In various embodiments, the subject has been suffering from uveitis for at least three months. For example, the at least one symptom of uveitis in the subject is improved after use of the composition. In various embodiments, the symptom of uveitis is selected from the group consisting of VH level, BCVA, macular edema, signs of ocular inflammation, retinal vessel leakage, CRT, and ocular inflammation in the anterior chamber.

In various embodiments of the use, the subject has been treated for at least three months with a corticosteroid. For example, the corticosteroid is prednisone. In various embodiments, the prednisone was administered from 15 to 80 mg/day.

In various embodiments, the subject was also administered methotrexate. For example, the methotrexate was administered from 6 to 25 mg/week.

In various embodiments, the subject is administered a corticosteroid. For example, the corticosteroid is prednisone. In various embodiments, the prednisone was administered from 15 to 80 mg/day.

In various embodiments, the subject is also administered methotrexate. For example, the methotrexate is administered from 6 to 25 mg/week.

In various embodiments, the subject achieves after 16 weeks a reduction in the VH level on the Miami 9 point scale of at least 2 steps or a reduction of corticosteroid dose to less than 10 mg per day.

In various embodiments, the subject achieves after 16 weeks a reduction in the VH level on the Miami 9 point scale of at least 2.

In various embodiments, the subject achieves after 16 weeks a reduction of corticosteroid dose to less than 10 mg per day.

In various embodiments, the subject experiences a reduction (e.g., greater than 20% reduction) in CRT, letters of BCVA (e.g., greater than 10 letters of BCVA), shows a reduction in retinal vessel leakage and/or an improvement in uveitis clinical assessment score. In various embodiments, the subject achieves after 16 weeks an improvement in BCVA. In various embodiments, he subject achieves after 16 weeks an improvement in CRT. In various embodiments, the subject achieves after 16 weeks an improvement in retinal vessel leakage.

In various embodiments, the subject achieves after 16 weeks an improvement in uveitis clinical assessment score.

In various embodiments, the antibody that specifically binds to the IL-6 receptor comprises a heavy chain variable region of sequence SEQ ID NO: 2 and the light chain variable region sequence of SEQ ID NO: 3.

In various embodiments, the antibody is administered from about 150 mg to about 200 mg per once every two weeks. In various embodiments, the antibody is administered at about 150 mg once every two weeks. In various embodiments, the antibody is administered at about 200 mg once every two weeks.

In various embodiments, the antibody is sarilumab. In various embodiments, the antibody is tocilizumab. For example, the tocilizumab is administered intravenously at from about 4 to about 8 mg/kg once every four weeks.

An aspect of the invention provides a composition for use in treatment of uveitis in a subject in need thereof, the composition comprising a therapeutically effective amount of an antibody, wherein the antibody comprises a heavy chain variable region of sequence SEQ ID NO:2 and the light chain variable region sequence of SEQ ID NO:3.

In various embodiments, the antibody is sarilumab.

In various embodiments, the uveitis is selected from the group consisting of intermediate uveitis, posterior uveitis and pan-uveitis.

In various embodiments, the uveitis is non-infectious uveitis. In various embodiments, the uveitis is systemic or idiopathic.

In various embodiments, the subject has a VH level greater than or equal to 2 on the Miami 9 step scale. In various embodiments, the subject has a VH level greater than or equal to 3, 4, 5, 6, 7 or 8 on the Miami 9 step scale. In various embodiments, the subject has a VH level greater than or equal to 4 on the Miami 9 step scale. In various embodiments, the subject is suffering from macular edema. In various embodiments, the subject has a CRT greater than 300 μm.

In various embodiments, the subject has other signs of intraocular inflammation. For example, the other signs of intraocular inflammation are selected from the group consisting of perivascular sheathing of retinal vessels and leakage of retinal vessels.

In various embodiments, the subject has been suffering from uveitis for at least three months.

In various embodiments, the at least one symptom of uveitis in the subject is improved after use of the composition. In various embodiments, the symptom of uveitis is selected from the group consisting of VH level, BCVA, macular edema, signs of ocular inflammation, CRT and ocular inflammation in the anterior chamber.

In various embodiments, the subject has been treated for at least three months with a corticosteroid. For example, the corticosteroid is prednisone. In various embodiments, the prednisone was administered from 15 to 80 mg/day.

In various embodiments, the subject was also administered methotrexate. For example, the methotrexate was administered from 6 to 25 mg/week.

In various embodiments, the subject is administered a corticosteroid. For example, the corticosteroid is prednisone. In various embodiments, the prednisone was administered from 15 to 80 mg/day.

In various embodiments, the subject is also administered methotrexate. For example, the methotrexate is administered from 6 to 25 mg/week.

In various embodiments, the subject achieves after 16 weeks a reduction in the VH level on the Miami 9 point scale of at least 2 steps or a reduction of corticosteroid dose to less than 10 mg per day.

In various embodiments, the subject achieves after 16 weeks a reduction in VH level on the Miami 9 point scale of at least 2.

In various embodiments, the subject achieves after 16 weeks a reduction of corticosteroid dose to less than 10 mg per day.

In various embodiments, the subject experiences a greater than 20% reduction in CRT, greater than 10 letters of BCVA, shows a reduction in retinal vessel leakage and/or an improvement in uveitis clinical assessment score.

In various embodiments, the subject achieves after 16 weeks an improvement in BCVA. In various embodiments, the subject achieves after 16 weeks an improvement in CRT. In various embodiments, the subject achieves after 16 weeks an improvement in retinal vessel leakage. In various embodiments, the subject achieves after 16 weeks an improvement in uveitis clinical assessment score.

An aspect of the invention provides use of a composition for the manufacture of a medicament for treating macular edema in a subject in need thereof, the composition comprising an effective amount of an antibody that specifically binds IL-6 receptor.

In various embodiments, the antibody that specifically binds to the IL-6 receptor comprises a heavy chain variable region of sequence SEQ ID NO:2 and the light chain variable region sequence of SEQ ID NO:3. For example, the antibody is sarilumab.

In various embodiments, subject is suffering from at least one symptom of macular edema selected from the group consisting of: ocular inflammation, impaired vision, impaired color recognition, tissue thickening, and leakage of ocular vessels. In various embodiments, at least one symptom of macular edema in the subject is improved after administering the antibody.

In various embodiments, the subject is suffering from cystoid macular edema. In various embodiments, the subject is suffering from diabetic retinopathy. In various embodiments, the macular edema is macular edema secondary to uveitis. For example, the uveitis is selected from the group consisting of intermediate uveitis, posterior uveitis and pan-uveitis.

In various embodiments, the subject has a CRT greater than 300 µm.

In various embodiments, at least one symptom of uveitis in the subject is improved after administering the antibody. In various embodiments, the symptom of uveitis is selected from the group consisting of: VH level, BCVA, signs of ocular inflammation, retinal vessel leakage, central retinal thickness, and ocular inflammation in the anterior chamber.

In various embodiments, the at least one symptom of macular edema and the at least one symptom of uveitis in the subject is improved after administering the antibody In various embodiments, the subject has been previously treated for at least three months with a corticosteroid. For example, the corticosteroid is prednisone.

In various embodiments, the prednisone was administered from 15 to 80 mg/day.

In various embodiments, the subject was also administered methotrexate. For example, the methotrexate was administered from 6 to 25 mg/week.

In various embodiments, the subject is also administered a corticosteroid. For example, the corticosteroid is prednisone. In various embodiments, the prednisone is administered from 15 to 80 mg/day.

In various embodiments, the subject is also administered methotrexate. For example, the methotrexate is administered from 6 to 25 mg/week.

In various embodiments, the subject achieves after 16 weeks a reduction in the VH level on the Miami 9 point scale of at least 2 steps or a reduction of corticosteroid dose to less than 10 mg per day.

In various embodiments, the subject achieves after 16 weeks a reduction in the VH level on the Miami 9 point scale of at least 2.

In various embodiments, the subject achieves after 16 weeks a reduction of corticosteroid dose to less than 10 mg per day.

In various embodiments, the subject experiences a greater than 20% reduction in CRT, greater than 10 letters of BCVA, shows a reduction in retinal vessel leakage and/or an improvement in uveitis clinical assessment score.

In various embodiments, the subject achieves after 16 weeks an improvement in BCVA.

In various embodiments, the subject achieves after 16 weeks an improvement in CRT.

In various embodiments, the subject achieves after 16 weeks an improvement in retinal vessel leakage.

In various embodiments, the subject achieves after 16 weeks an improvement in a clinical assessment score.

In various embodiments, the antibody is administered subcutaneously.

In various embodiments, the antibody is administered from about 150 to about 200 mg once every two weeks. For example, the antibody is administered at about 150 mg once every two weeks. In various embodiments, the antibody is administered at about 200 mg once every two weeks.

In various embodiments, the antibody is tocilizumab. For example, the tocilizumab is administered intravenously from about 4 to about 8 mg/kg once every four weeks. In various embodiments, the tocilizumab is administered subcutaneously at about 162 mg once a week or once every two weeks.

An aspect of the invention provides use of an antibody for the manufacture of a medicament for treating uveitis and/or macular edema in a subject, wherein the antibody specifically binds IL-6 receptor, optionally wherein the subject has a VH level greater than or equal to 2 on the Miami 9 step scale or wherein the subject has a CRT greater than 300 µm.

An aspect of the invention provides use of a composition for the manufacture of a medicament for treating uveitis in a subject in need thereof, wherein the composition comprises an effective amount of an antibody that specifically binds IL-6 receptor, wherein the subject has a VH level greater than or equal to 2 on the Miami 9 step scale or wherein the subject has a CRT greater than 300 µm.

In various embodiments, the subject has a VH level greater than or equal to 3, 4, 5, 6, 7, or 8 on the Miami 9 step scale.

In various embodiments, the subject has a VH level greater than or equal to 4 on the Miami 9 step scale.

In various embodiments, the uveitis is selected from the group consisting of intermediate uveitis, posterior uveitis and pan-uveitis. In various embodiments, the uveitis is non-infectious uveitis. In various embodiments, the uveitis is systemic or idiopathic.

In various embodiments, the subject is suffering from macular edema, for example cystoid macular edema.

In various embodiments, the subject has a CRT greater than 300 µm.

In various embodiments, the subject has other signs of intraocular inflammation. For example, the other signs of intraocular inflammation are selected from the group consisting of perivascular sheathing of retinal vessels and leakage of retinal vessels.

In various embodiments, the subject has been suffering from uveitis for at least three months.

In various embodiments, at least one symptom of uveitis in the subject is improved. For example, the symptom of uveitis is selected from the group consisting of VH level, BCVA, macular edema, signs of ocular inflammation, retinal vessel leakage, CRT, and ocular inflammation in the anterior chamber.

In various embodiments, the subject has been treated for at least three months with a corticosteroid. For example, the corticosteroid is prednisone. In various embodiments, the prednisone was administered from 15 to 80 mg/day.

In various embodiments, the subject was also administered methotrexate. For example, methotrexate was administered from 6 to 25 mg/week.

In various embodiments, the subject is administered a corticosteroid. For example, the corticosteroid is prednisone. In various embodiments, the prednisone was administered from 15 to 80 mg/day.

In various embodiments, the subject is also administered methotrexate. For example, the methotrexate is administered from 6 to 25 mg/week.

In various embodiments, the subject achieves after 16 weeks a reduction in the VH level on the Miami 9 point scale of at least 2 steps or a reduction of corticosteroid dose to less than 10 mg per day.

In various embodiments, the subject achieves after 16 weeks a reduction in the VH level on the Miami 9 point scale of at least 2. In various embodiments, the subject achieves after 16 weeks a reduction of corticosteroid dose to less than 10 mg per day. In various embodiments, the subject experiences a greater than 20% reduction in CRT, greater than 10 letters of BCVA, shows a reduction in retinal vessel leakage and/or an improvement in uveitis clinical assessment score.

In various embodiments, the subject achieves after 16 weeks an improvement in BCVA. In various embodiments, the subject achieves after 16 weeks an improvement in CRT. In various embodiments, the subject achieves after 16 weeks an improvement in retinal vessel leakage. In various embodiments, the subject achieves after 16 weeks an improvement in uveitis clinical assessment score.

In various embodiments, the antibody that specifically binds to the IL-6 receptor comprises a heavy chain variable region of sequence SEQ ID NO:2 and the light chain variable region sequence of SEQ ID NO:3.

In various embodiments, the antibody is administered from about 150 to about 200 mg once every two weeks. For example, the antibody is administered at about 150 mg once every two weeks. In various embodiments, the antibody is administered at about 200 mg once every two weeks.

In various embodiments, the antibody is sarilumab.

In various embodiments, the antibody is tocilizumab. For example, the tocilizumab is administered intravenously from about 4 to about 8 mg/kg once every four weeks. In various embodiments, the tocilizumab is administered subcutaneously at about 162 mg once a week or once every two weeks.

An aspect of the invention provides use of an antibody for the manufacture of a medicament for treating uveitis and/or macular edema in a subject, wherein the antibody comprises a heavy chain variable region of sequence SEQ ID NO:2 and the light chain variable region sequence of SEQ ID NO:3.

An aspect of the invention provides use of a composition for the manufacture of a medicament for treating uveitis in a subject in need thereof, wherein the composition comprises a therapeutically effective amount of an antibody, wherein the antibody comprises a heavy chain variable region of sequence SEQ ID NO:2 and the light chain variable region sequence of SEQ ID NO:3. In various embodiments, the antibody is sarilumab.

In various embodiments, the uveitis is selected from the group consisting of intermediate uveitis, posterior uveitis and pan-uveitis. In various embodiments, the uveitis is non-infectious uveitis. In various embodiments, the uveitis is systemic or idiopathic.

In various embodiments, the subject has a VH level greater than or equal to 2 on the Miami 9 step scale.

In various embodiments, the subject has a VH level greater than or equal to 3, 4, 5, 6, 7 or 8 on the Miami 9 step scale. In various embodiments, the subject has a VH level greater than or equal to 4 on the Miami 9 step scale.

In various embodiments, the subject is suffering from macular edema.

In various embodiments, the subject has a CRT greater than 300 µm.

In various embodiments, the subject has other signs of intraocular inflammation. For example, the other signs of intraocular inflammation are selected from the group consisting of perivascular sheathing of retinal vessels and leakage of retinal vessels.

In various embodiments, the subject has been suffering from uveitis for at least three months.

In various embodiments, at least one symptom of uveitis in the subject is improved. In various embodiments, the symptom of uveitis is selected from the group consisting of VH level, BCVA, macular edema, signs of ocular inflammation, CRT and ocular inflammation in the anterior chamber.

In various embodiments, the subject has been treated for at least three months with a corticosteroid. For example, the corticosteroid is prednisone.

In various embodiments, the prednisone was administered from 15 to 80 mg/day. In various embodiments, the subject was also administered methotrexate. For example, the methotrexate was administered from 6 to 25 mg/week.

In various embodiments, the subject is administered a corticosteroid. For example, the corticosteroid is prednisone. In various embodiments, the prednisone was administered from 15 to 80 mg/day.

In various embodiments, the subject is also administered methotrexate. For example, the methotrexate is administered from 6 to 25 mg/week.

In various embodiments, the subject achieves after 16 weeks a reduction in the VH level on the Miami 9 point scale of at least 2 steps or a reduction of corticosteroid dose to less than 10 mg per day.

In various embodiments, the subject achieves after 16 weeks a reduction in VH level on the Miami 9 point scale of at least 2.

In various embodiments, the subject achieves after 16 weeks a reduction of corticosteroid dose to less than 10 mg per day.

In various embodiments, the subject experiences a greater than 20% reduction in CRT, greater than 10 letters of BCVA, shows a reduction in retinal vessel leakage and/or an improvement in uveitis clinical assessment score.

In various embodiments, the subject achieves after 16 weeks an improvement in BCVA.

In various embodiments, the subject achieves after 16 weeks an improvement in CRT.

In various embodiments, the subject achieves after 16 weeks an improvement in retinal vessel leakage.

In various embodiments, the subject achieves after 16 weeks an improvement in uveitis clinical assessment score.

EXAMPLES OF EMBODIMENTS OF THE INVENTION ARE LISTED BELOW

Embodiment 1

A method for treating uveitis and/or macular edema in a subject in need thereof comprising administering an effective amount of an antibody that specifically binds IL-6 receptor.

Embodiment 2

The method of Embodiment 1, wherein the subject has a vitreous haze level (VH level) greater than or equal to 2 on the Miami 9 step scale.

Embodiment 3

The method of Embodiment 1 or 2, wherein the subject has a central retinal thickness (CRT) greater than 300 µm.

Embodiment 4

The method of any of the preceding embodiments, wherein the subject has a VH level greater than or equal to 3, 4, 5, 6, 7 or 8 on the Miami 9 step scale.

Embodiment 5

The method of any one of the preceding Embodiments, wherein the subject has a VH level greater than or equal to 4 on the Miami 9 step scale.

Embodiment 6

The method of any of the preceding Embodiments, wherein the uveitis is selected from the group consisting of intermediate uveitis, posterior uveitis and pan-uveitis.

Embodiment 7

The method of any of the preceding Embodiments, wherein the uveitis is non-infectious uveitis.

Embodiment 8

The method of any of the preceding Embodiments, wherein the uveitis is systemic or idiopathic.

Embodiment 9

The method of any of the preceding Embodiments, wherein the subject is suffering from macular edema.

Embodiment 10

The method of any of the preceding Embodiments, wherein the subject has a CRT greater than 300 μm.

Embodiment 11

The method of any of the preceding Embodiments, wherein the subject has other signs of intraocular inflammation.

Embodiment 12

The method of Embodiment 11, wherein the other signs of intraocular inflammation are selected from the group consisting of perivascular sheathing of retinal vessels and leakage of retinal vessels.

Embodiment 13

The method of any of the preceding Embodiments, wherein the subject has been suffering from uveitis for at least three months.

Embodiment 14

The method of Embodiment 13, wherein at least one symptom of uveitis and/or macular edema in the subject is improved.

Embodiment 15

The method of Embodiment 14, wherein the symptom of uveitis is selected from the group consisting of elevated VH level, reduced best corrected visual acuity (BCVA), macular edema, signs of ocular inflammation, retinal vessel leakage, CRT and ocular inflammation in the anterior chamber.

Embodiment 16

The method of any of the preceding Embodiments, wherein the subject has been treated for at least three months with a corticosteroid.

Embodiment 17

The method of Embodiment 16, wherein the corticosteroid is prednisone.

Embodiment 18

The method of Embodiment 17, wherein the prednisone was administered from 15 to 80 mg/day.

Embodiment 19

The method of any of the preceding Embodiments, wherein the subject was also administered methotrexate.

Embodiment 20

The method of Embodiment 19, wherein the methotrexate was administered from 6 to 25 mg/week.

Embodiment 21

The method of any of the preceding Embodiments, wherein the subject is administered a corticosteroid.

Embodiment 22

The method of Embodiment 21, wherein the corticosteroid is prednisone.

Embodiment 23

The method of Embodiment 22, wherein the prednisone was administered from 15 to 80 mg/day.

Embodiment 24

The method of any of the preceding Embodiments, wherein the subject is also administered methotrexate.

Embodiment 25

The method of Embodiment 24, wherein the methotrexate is administered from 6 to 25 mg/week.

Embodiment 26

The method of any one of Embodiments 16-18 or 21-23, wherein the subject achieves after 16 weeks:
- a reduction in the VH level on the Miami 9 point scale of at least 2 steps, or
- a reduction of corticosteroid dose to less than 10 mg per day.

Embodiment 27

The method of any of the preceding Embodiments, wherein the subject achieves after 16 weeks a reduction in the VH level on the Miami 9 point scale of at least 2 steps.

Embodiment 28

The method of any one of Embodiments 16-18 or 21-23, wherein the subject achieves after 16 weeks a reduction of corticosteroid dose to less than 10 mg per day.

Embodiment 29

The method of any of the preceding Embodiments, wherein the subject experiences:
experiences a greater than 20% reduction in CRT,
greater than 10 letters of improvement in BCVA,
a reduction in retinal vessel leakage, and/or
an improvement in uveitis clinical assessment score.

Embodiment 30

The method of Embodiment 29, wherein the subject achieves after 16 weeks an improvement in BCVA.

Embodiment 31

The method of Embodiment 29, wherein the subject achieves after 16 weeks an improvement in CRT.

Embodiment 32

The method of Embodiment 39, wherein the subject achieves after 16 weeks an improvement in retinal vessel leakage.

Embodiment 33

The method of Embodiment 29, wherein the subject achieves after 16 weeks an improvement in uveitis clinical assessment score.

Embodiment 34

The method of any of the preceding Embodiments, wherein the antibody that specifically binds to the IL-6 receptor comprises a heavy chain variable region of sequence SEQ ID NO:2 and the light chain variable region sequence of SEQ ID NO:3.

Embodiment 35

The method of Embodiment 34, wherein the antibody is administered at about 200 mg per two weeks.

Embodiment 36

The method of any of the preceding Embodiments, wherein the antibody is sarilumab.

Embodiment 37

The method of any of Embodiments 1-33, wherein the antibody is tocilizumab.

Embodiment 38

The method of Embodiment 37, wherein the tocilizumab is administered from 4 to 8 mg/kg.

Embodiment 39

A method of treating uveitis and/or macular edema in a subject in need thereof comprising administering to the subject a therapeutically effective amount of an antibody, wherein the antibody comprises a heavy chain variable region of sequence SEQ ID NO:2 and the light chain variable region sequence of SEQ ID NO:3.

Embodiment 40

The method of Embodiment 39, wherein the antibody is sarilumab.

Embodiment 41

The method of any of Embodiments 39 or 40, wherein the uveitis is selected from the group consisting of intermediate uveitis, posterior uveitis and pan-uveitis.

Embodiment 42

The method of any of Embodiments 39-41, wherein the uveitis is non-infectious uveitis.

Embodiment 43

The method of any of Embodiments 39-42, wherein the uveitis is systemic or idiopathic.

Embodiment 44

The method of any of Embodiments 39-43, wherein the subject has a VH level greater than or equal to 2 on the Miami 9 step scale.

Embodiment 45

The method of Embodiment 44, wherein the subject has a vitreous haze (VH) level greater than or equal to 3, 4, 5, 6, 7 or 8 on the Miami 9 step scale.

Embodiment 46

The method of Embodiment 44, wherein the subject has a vitreous haze (VH) level greater than or equal to 4 on the Miami 9 step scale.

Embodiment 47

The method of any of Embodiments 39-46, wherein the subject is suffering from macular edema.

Embodiment 48

The method of any of Embodiments 39-47, wherein the subject has a CRT greater than 300 μm.

Embodiment 49

The method of any of Embodiments 39-48, wherein the subject has other signs of intraocular inflammation.

Embodiment 50

The method of Embodiment 49, wherein the other signs of intraocular inflammation are selected from the group consisting of perivascular sheathing of retinal vessels and leakage of retinal vessels.

Embodiment 51

The method of any of Embodiments 39-50, wherein the subject has been suffering from uveitis for at least three months.

Embodiment 52

The method of any of Embodiments 39-51, wherein at least one symptom of uveitis in the subject is improved.

Embodiment 53

The method of Embodiment 52, wherein the symptom of uveitis is selected from the group consisting of elevated VH level, reduced BCVA, macular edema, signs of ocular inflammation, CRT and ocular inflammation in the anterior chamber.

Embodiment 54

The method of any of Embodiments 39-53, wherein the subject has been treated for at least three months with a corticosteroid.

Embodiment 55

The method of Embodiment 54, wherein the corticosteroid is prednisone.

Embodiment 56

The method of Embodiment 55, wherein the prednisone is administered from 15-to 80 mg/day.

Embodiment 57

The method of any of Embodiments 39-56, wherein the subject was also administered methotrexate.

Embodiment 58

The method of Embodiment 58, wherein the methotrexate is administered from 6- to 25 mg/week.

Embodiment 59

The method of any of Embodiments 39-58, wherein the subject is administered a corticosteroid.

Embodiment 60

The method of Embodiment 59, wherein the corticosteroid is prednisone.

Embodiment 61

The method of Embodiment 60, wherein the prednisone is administered from 15 to 80 mg/day.

Embodiment 62

The method of any of Embodiments 39-61, wherein the subject is also administered methotrexate.

Embodiment 63

The method of Embodiment 62, wherein the methotrexate is administered from 6 to 25 mg/week.

Embodiment 64

The method of any one of Embodiments 54-56 or 59-60, wherein the subject achieves after 16 weeks a reduction in the VH level on the Miami 9 point scale of at least 2 steps; or
a reduction of corticosteroid dose to less than 10 mg per day.

Embodiment 65

The method of any of Embodiments 39-64, wherein the subject achieves after 16 weeks a reduction in VH level on the Miami 9 point scale of at least 2.

Embodiment 66

The method of any one of Embodiments 54-56 or 59-60, wherein the subject achieves after 16 weeks a reduction of corticosteroid dose to less than 10 mg per day.

Embodiment 67

The method of any of Embodiments 39-66, wherein the subject experiences:
a greater than 20% reduction in CRT,
greater than 10 letters of improvement in BCVA,
a reduction in retinal vessel leakage, and/or
an improvement in uveitis clinical assessment score.

Embodiment 68

The method of Embodiment 67, wherein the subject achieves after 16 weeks an improvement in BCVA.

Embodiment 69

The method of Embodiment 67, wherein the subject achieves after 16 weeks an improvement in CRT.

Embodiment 70

The method of Embodiment 67, wherein the subject achieves after 16 weeks an reduction in retinal vessel leakage.

Embodiment 71

The method of Embodiment 66, wherein the subject achieves after 16 weeks an improvement in uveitis clinical assessment score.

DETAILED DESCRIPTION

The disclosure provides pharmaceutical compositions and methods of using these compositions for the treatment of uveitis and/or macular edema, and the improvement of at least one symptom of one or both of these disorders. These compositions include at least one antibody that specifically binds human interleukin-6 receptor (hIL-6R) and, optionally, at least one additional therapeutic agent such as methotrexate or a corticosteroid.

Anti-hIL-6R Antibodies

The present disclosure includes methods that comprise administering to a patient a human antibody, or an antigen-binding fragment thereof, that binds specifically to hIL-6R. As used herein, the term "hIL-6R" means a human cytokine receptor that specifically binds human interleukin-6 (IL-6). In certain embodiments, the antibody that is administered to the patient binds specifically to the extracellular domain of hIL-6R.

The extracellular domain of hIL-6R is shown in the amino acid sequence of SEQ ID NO:1. The sequence of SEQ ID NO: 1 is MVAVGCALLAALLAAPGAALAPRRCPAQE-VARGVLTSLPGDSVTLTCPGVEPEDNATV HWVLRKPAAGSHPSRWAGMGRRLLLRSVQLHDSG-NYSCYRAGRPAGTVHLLVDVPP EEPQLSCFRKSPL-SNVVCEWGPRSTPSLTTKAVLLVRKFQNSPAE-DFQEPCQYSQES QKFSCQLAVPEGDSSFYIVSMCVASSVG-SKFSKTQTFQGCGILQPDPPANITVTAVARN PRWLSVTWQDPHSWNSSFYRLRFELRYRAER-SKTFTTWMVKDLQHHCVIHDAWSGL RHVVQL-RAQEEFGQGEWSEWSPEAMGTPWTESRSPPAE-NEVSTPMQALTTNKDDD NILFRDSANATSLPVQD.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_{H1}$; (ii) $V_H$-$C_{H2}$; (iii) $V_H$-$C_{H3}$; (iv) $V_H$-$C_{H1}$-$C_{H2}$; (V) $V_H$-$C_{H1}$-$C_{H2}$-$C_{H3}$, (vi) $V_H$-$C_{H2}$-$C_{H3}$, (vii) $V_H$-$C_L$; (viii) $V_L$-$C_{H1}$; (ix) $V_L$-$C_{H2}$, (x) $V_L$-$C_{H3}$, (xi) $V_L$-$C_{H1}$-$C_{H2}$; (xii) $V_L$-$C_{H1}$-$C_{H2}$-$C_{H3}$, (xiii) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "specifically binds," means that an antibody or antigen-binding fragment thereof forms a complex with an antigen that is relatively stable under physiologic conditions. Specific binding can be characterized by a dissociation constant of at least about $1 \times 10^{-6}$ M or smaller. In other embodiments, the dissociation constant is at least about $1 \times 10^{-7}$ M, $1 \times 10^{-8}$ M, or $1 \times 10^{-9}$ M. Methods for determining whether two molecules specifically bind are well known in the art and include, for example, equilibrium dialysis, surface plasmon resonance, and the like.

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In specific embodiments, the antibody or antibody fragment for use in the method of the invention may be a multispecific antibody, which may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bispecific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise an Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

In other specific embodiments, the antibody is sarilumab (SAR153191). The heavy chain variable region of sarilumab comprises the sequence of SEQ ID NO:2.

The light chain variable region of sarilumab comprises the sequence of SEQ ID NO:3.

A "neutralizing" or "blocking" antibody, as used herein, is intended to refer to an antibody whose binding to hIL-6R results in inhibition of the biological activity of hIL-6. This inhibition of the biological activity of hIL-6 can be assessed by measuring one or more indicators of hIL-6 biological activity known to the art, such as hIL-6-induced cellular activation and hIL-6 binding to hIL-6R (see examples below).

The fully-human anti-IL-6R antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the VH and/or VL domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The term "epitope" refers to an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sufonyl groups on the antigen.

The anti-hIL-6R antibody can be sarilumab (SAR153191). In one embodiment, sarilumab is defined as an antibody comprising the heavy chain variable region of SEQ ID NO:2 and the light chain variable region of SEQ ID NO:3.

The amino acid sequence of SEQ ID NO: 2 is EVQLVESGGGLVQPGRSLRLSCAASRFTFDDYAMHWVRQAPGKGLEWVSGISWNSG RIGYADSVKGRFTISRDNAENSLFLQMNGLRAEDTALYYCAKGRDSFDIWGQGTMVTV SS.

The amino acid sequence of SEQ ID NO: 3 is DIQMTQSPSSVSASVGDRVTITCRASQGISSWLAWYQQKPGKAPKLLIYGASSLESGV PSRFSGSGSGTDFTLTISSLQPEDFASYYCQQANSFPYTFGQGTKLEIK.

In other embodiments, sarilumab is defined as an antibody comprising the heavy chain comprising the amino acid sequence of SEQ ID NO:4 and the light chain comprising the amino acid sequence of SEQ ID NO:5.

The amino acid sequence of SEQ ID NO: 4 is EVQLVESGGGLVQPGRSLRLSCAAS RFTFDDYAMHWVRQAPGKGLEWVSG ISWNSGRIGYADSVKGRFTISRDNAENSLFLQMNGL RAEDTALYYCAKGRDSFDIWGQGTMVTV SSASTKGPSVFPLAPSSKSTSGGTAALGCLVKDYF PEPVTVSWNSGALTSGVHTFPAV LQSSGLYSLSSVVTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAP IEKTISKAKGQPREPQV YTLPPSRDELTKNQVSLTCLVKGFYPSDIAVEWESNGQPENNYKTTPPVLDSDGSFFLY SKLTVDKSRWQQGNVFSCSVMHEALHNHYTQKSLSLSPGK.

The amino acid sequence of SEQ ID NO: 5 is DIQMTQSPSSVSASVGDRVTITCRAS QGISSWLAWYQQKPGKAPKLLIYGASSL ESGVPSRFSGSGSGTDFTLTISSLQPEDFASYYC QQANSFPYTFGQGTKLE IKRTVAAP SVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC. The anti-hIL6R antibody can also be tocilizumab. Tocilizumab is also known as "humanized PM-1 antibody" or "hMP1", and was obtained by grafting the complementarity determining regions (CDRs) of a mouse antibody PM-1 (Hirata et al., J. Immunology (1989) 143, 2900-2906), to a human antibody (International Patent Application WO 92/19759). WO96/11020 shows that a humanized PM1 antibody is effective in an animal model for rheumatoid arthritis. Tocilizumab is marketed under the brand name Actemra®.

Dosage Ranges

As used herein, "administered from about X to about Y mg" means that the referred to substance is administered at any value within the stated range including the endpoints of the range. For example, "the dose of anti-hIL-6R antibody administered to the patient is from 10 mg to 500 mg," includes administration of 10 mg of the anti-hIL-6R antibody, 500 mg of the anti-hIL-6R antibody and all doses in between.

Corticosteroids

Corticosteroids include prednisone, hydrocortisone, hydrocortisone acetate, cortisone acetate, tixocortol pivalate, prednisolone and methylprednisolone. According to the compositions and methods of the disclosure, corticosteroids can be administered as follows. The corticosteroid can be administered from 15 to 80 mg orally daily. In certain embodiments, the corticosteroid can be administered from 15 to 20, from 20 to 50, and from 35 to 80 mg per day. In other embodiments, the corticosteroid is administered at 15, 20, 25, 30, 35, 40, 45, 50, 55, 60, 65, 70, 75 or 80 mg per day. According to certain embodiments, the corticosteroid is prednisone.

According to other embodiments, the corticosteroid can also be selected from triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate.

Methotrexate

Methotrexate can be administered from 6 to 25 mg per week orally or intramuscularly. In another embodiment, methotrexate is administered from 6 to 25 mg/week orally or intramuscularly for patients who are from the Asia-Pacific region or who are descended from people who are from the Asia-Pacific region. The Asia-Pacific region includes Taiwan, South Korea, Malaysia, Philippines, Thailand and India. In certain embodiments, methotrexate is administered from 6 to 12, from 10 to 15, from 15 to 20 and from 20 to 25 mg per week. In other embodiments, methotrexate is administered at 6, 7, 8, 9, 10, 11, 12, 13, 14, 15, 16, 17, 18, 19, 20, 21, 22, 23, 24 or 25 mg per week.

Uveitis

Uveitis as used herein refers to any intraocular inflammatory disease or disorder. See "Taber's Cyclopedic Medical Dictionary", 1997 (18$^{th}$ edition), edited by Clayton L. Thomas, M. D., M.PH., published by F. A. Davis Company, Philadelphia, Pa. Different types of uveitis are described below. Both uveal tract structures (e.g., iris, ciliary body and choroid) and nonuveal parts of the eye (e.g., retina and cornea) may be involved in uveitis. Uveitis may include iritis (i.e., inflammation of the iris), cyclitis (i.e., inflammation of the ciliary body), panuveitis (i.e., inflammation of the entire uveal vascular layer of the eye), posterior uveitis and anterior uveitis. Intermediate uveitis, also called peripheral uveitis, is centered in the area immediately behind the iris and lens in the region of the ciliary body and pars plana, and is also termed "cyclitis" and "pars planitis." See also U.S. Pat. Nos. 9,139,646; 8,895,521; and U.S. patent publication number 20090082288 A1, each of which is incorporated herein in its entirety. Uveitis may be acute (i.e., signs and symptoms occur suddenly and last for a short period of time, for example, days or weeks) or can be chronic (i.e., onset is gradual and lasts longer than acute uveitis, for example for weeks, months or years).

"Posterior uveitis" is often referred to as chorioretinitis, which is a form of uveitis involving inflammation of the choroid and retina. See also Suttorp-Schulten et al., 1996 Ocul Immunol Inflamm. 4(4): pages 207-217. "Anterior uveitis" as used herein refers to iridocyclitis, which is a disorder characterized by inflammation of the iris and the ciliary body and/or iritis. Anterior uveitis typically results in symptoms such as pain, redness, photophobia, and decreased vision. Signs of anterior uveitis include pupillary miosis and injections of the conjunctiva adjacent to the cornea, so-called perilimbal flush. See also Gordon et al., 1998 J Clin Immunol. 18(4): pages 264-271. "Diffuse" uveitis refers to a type of uveitis characterized by inflammation involving all parts of the eye, including anterior, intermediate, and posterior structures. See Huang et al., "Ocular Inflammatory Disease and Uveitis Manual: Diagnosis and Treatment"

The inflammatory products (e.g., cells, fibrin, excess proteins) of ocular inflammation may in various embodiments be found in the fluid spaces of the eye. For example, the inflammatory products may be found in the anterior chamber, posterior chamber and vitreous space.

Uveitis may occur following surgical or traumatic injury to the eye; as a component of an autoimmune disorder (for example such as rheumatoid arthritis, Bechet's disease, sarcoidosis, etc.), as an isolated immune mediated ocular disorder (such as pars planitis or iridocyclitis), as a disease unassociated with known etiologies, and following certain systemic diseases which cause antibody-antigen complexes to be deposited in the uveal tissues. Uveitis includes ocular inflammation associated with Bechet's disease, sarcoidosis, Vogt-Koyanagi-Harada syndrome, etc. In various embodiments, non-infectious uveitis occurs in the absence of an infectious agent.

Macular Edema

"Macular edema" as used herein refers to an accumulation of fluid within the macula part of the retina. The fluid affects the blood supply to the macular and/or retina, creating a negative effects on vision. Symptoms of macular edema include visual acuity deterioration, micropsy, metamorphopsy, reduced colour perception, as well as central or paracentral scotoma. See U.S. Pat. No. 6,046,223. Different types of macular edema exist including cystoid macular edema, which is a disorder which affects the central retina or macula. Cystoid macular edema is often diagnosed by the presence of multiple cyst-like (cystoid) areas of fluid appear in the macula that cause retinal swelling or edema. In various embodiments, the subject is suffering from diabetic retinopathy which may cause macular edema.

Therapeutic Administration and Formulations

The methods described herein comprise administering a therapeutically effective amount of an anti-hIL-6R antibody to a subject. As used herein, the phrase "therapeutically effective amount" means a dose of the therapeutic that results in treatment of uveitis and/or macular edema. As used herein, "treating" refers to causing a detectable improvement in one or more symptoms associated with uveitis and/or macular edema, or causing a biological effect (e.g., a decrease in the level of a particular biomarker) that is correlated with the underlying pathologic mechanism(s) giving rise to the condition or symptom(s). For example, the following symptoms or conditions are associated with uveitis and macular edema: elevated vitreous haze (VH) level, diminished best corrected visual acuity (BCVA), elevated amounts of fluid in the macula, signs of ocular inflammation, retinal vessel leakage, elevated central retinal thickness (CRT), and ocular inflammation in the anterior chamber. More specifically, symptoms that are associated with macular edema include blurry or wavy vision near the center of the field of vision, ocular inflammation, impaired vision, impaired color recognition, tissue thickening, and leakage of ocular vessels. In certain embodiments, the symptoms of macular edema are improved by reducing excess fluid in the macula.

Vitreous Haze (VH)

Vitreous haze will be evaluated by the Miami 9-step scale (grades 0 through 8) (see, Davis J L, et al. Am J Ophthalmol. 2010; 150(5): 637-41). Vitreous haze is the obscuration of fundus details by vitreous cells and protein exudation. It impacts vision more profoundly than anterior chamber inflammation and is therefore used commonly as an outcome measure for clinical trials involving intermediate, posterior, or panuveitis.

BCVA (ETDRS Letters Score)

The visual acuity (VA) may be evaluated using the BCVA score, assessed using Early Treatment Diabetic Retinopathy Study (ETDRS) standardized protocol. Best corrected visual acuity can be measured at each visit.

Central Retinal Thickness (CRT)

The central retinal thickness (CRT) can be measured by Spectral Domain optical coherence tomography (SD-OCT). Spectral domain optical coherence tomography can be performed using standardized techniques.

Clinical Assessment Score

A patient may be identified as "active" based on one of the following criteria at baseline (Index Variable) and evaluated on that parameter following treatment to determine if the patient reached an "inactive" state after treatment: VH, CRT, and BCVA. Secondary Variables: Clinical Assessment Score (CAS) [regardless of parameter for activity] Improved: I, Not Changed: N, Worse: W.

Improved: a score of I (Improved) is assigned for what is considered to be a clinically relevant improvement. A score of N (Not Changed) is assigned when there is no change or when change is thought not to be clinically important. A score of W (Worse) is assigned when a change places the study participant at a short term risk of vision loss and requires withdrawal from the study.

| Index Variable | Active | Inactive |
| --- | --- | --- |
| Clinical VH assessment | >4 | 0 |
| Clinical CRT assessment | >=300 | <300 |
| BCVA evaluation | <70 | >=70 |

When several variables are available for a type of uveitis, the variable with the worst baseline status (clinical judgment) may be selected as index.

| | Success Definition |
| --- | --- |
| Clinical VH assessment | Study eye 2 step reduction according to change from baseline |
| Clinical CRT assessment | Study eye CRT - reduction >=20% compared to baseline for patients with macular edema |
| Anterior chamber | 2 step |
| BCVA evaluation | Study eye BCVA - improvement change from baseline >=10 letters |

All signs of inflammation other than the index variable for a given patient may be considered as secondary variable for that patient. Fundamental signs of inflammation not chosen as the index variable may be considered secondary variables. Grading is used primarily in stopping rules; improvement in a secondary variable does not qualify as an improvement even if the secondary variable is a fundamental sign of inflammation (but one not chosen as the index variable for that patient).

In certain embodiments, the VH level is reduced by 2 points on the Miami 9 point scale. According to other embodiments, the VH level is reduced by 1, 2, 3, 4, 5, 6, 7, 8 or 9 points on the Miami 9 point scale. According to other embodiments, the VH level is reduced by 1-2, 1-3, 1-4 2-4 or 3-5 points on the Miami 9 point scale.

In certain embodiments, BCVA is improved by 10 letters on an EDTRS chart. According to other embodiments, BCVA is improved by 1, 2, 3, 4, 5, 6, 7, 8, 9, 10, 11, 12, 13, 14, 15, 16, 17, 18, 19 or 20 letters on an EDTRS chart. According to other embodiments, BCVA is improved by 5-15, 7-13 or 8-12 letters on an EDTRS chart.

In other embodiments, a therapeutically effective amount reduces the dose of corticosteroid administered to a subject. In certain embodiments, that dose of corticosteroid is reduced to less than 100, 90, 80, 70, 60, 50, 40, 30, 20, 10, 5 or 1 mg per day. In certain embodiments, the corticosteroid is prednisone.

In accordance with the methods of the present invention, a therapeutically effective amount of anti-hIL-6R antibody that is administered to the patient will vary depending upon the age and the size (e.g., body weight or body surface area) of the patient as well as the route of administration and other factors well known to those of ordinary skill in the art. In certain embodiments, the dose of anti-hIL-6R antibody administered to the patient is from about 10 mg to about 500 mg. For example, the present invention includes methods wherein about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300, about 325 mg, about 350 mg, about 375 mg, about 400 mg, about 425 mg, about 450 mg, about 475 mg, about 500 mg, or more of anti-hIL-6R antibody is administered to the patient per week.

In various embodiments, the hIL-6R antibody is administered from 100 to 200 mg once a week. In an embodiment, the hIL-6R antibody is administered at 100 mg once a week. In an embodiment, the hIL-6R antibody is administered at 150 mg once a week. In an embodiment, the hIL-6R antibody is administered at 200 mg once a week. In one embodiment, the hIL-6R antibody is administered from 100 to 150 mg once a week. In another embodiment, the hIL-6R antibody is administered from 100 to 200 mg once every two weeks. In another embodiment, the hIL-6R antibody is administered from 150 to 200 mg once every two weeks. In other embodiments, the hIL-6R antibody is administered at about 100 or about 150 mg once a week. In other embodiments, the hIL-6R antibody is administered at about 100, 150 or 200 mg once every two weeks. In an embodiment, the hIL-6R antibody is administered at 100 mg once every two weeks. In an embodiment, the hIL-6R antibody is administered at 150 mg once every two weeks. In an embodiment, the hIL-6R antibody is administered at 200 mg once every two weeks. According to some of these embodiments, the hIL-6R antibody is administered subcutaneously. According to some of these embodiments, the hIL-6R antibody is sarilumab.

In one embodiment, the hIL-6R antibody is administered from about 100 to about 150 mg once a week. In another embodiment, the hIL-6R antibody is administered from about 100 to about 200 mg once every two weeks. In another embodiment, the hIL-6R antibody is administered from about 150 to about 200 mg once every two weeks. According to some of these embodiments, the hIL-6R antibody is administered subcutaneously. According to some of these embodiments, the hIL-6R antibody is sarilumab.

In one embodiment, the hIL-6R antibody is administered at about 162 mg once a week. In another embodiment, the hIL-6R antibody is administered at about 162 mg once every two weeks. In another embodiment, the hIL-6R antibody is administered at 162 mg once a week. In another embodiment, the hIL-6R antibody is administered at 162 mg once every two weeks. According to some of these embodiments, the hIL-6R antibody is administered subcutaneously. According to some of these embodiments, the hIL-6R antibody is tocilizumab.

The amount of anti-hIL-6R antibody that is administered to the patient may be expressed in terms of milligrams of antibody per kilogram of patient body weight (i.e., mg/kg). For example, the methods of the present invention include administering an anti-hIL-6R antibody to a patient at a daily dose from about 0.01 to about 100 mg/kg, from about 0.1 to about 50 mg/kg, or from about 1 to about 10 mg/kg of patient body weight. In certain embodiments, the anti-hIL6R antibody is tocilizumab and is administered from about 4 mg/kg to about 8 mg/kg. In other embodiments, the anti-hIL6R antibody is tocilizumab and is administered from 4 mg/kg to 8 mg/kg. In some of these embodiments, tocilizumab is administered intravenously.

The methods of the present invention include administering multiple doses of an anti-hIL-6R antibody to a patient over a specified time course. For example, the anti-hIL-6R antibody can be administered about 1 to 5 times per day, about 1 to 5 times per week, about 1 to 5 times per month or about 1 to 5 times per year. In certain embodiments, the methods of the invention include administering a first dose of anti-hIL-6R antibody to a patient at a first time point, followed by administering at least a second dose of anti-hIL-6R antibody to the patient at a second time point. The first and second doses, in certain embodiments, may contain the same amount of anti-hIL-6R antibody. For instance, the first and second doses may each contain from about 10 mg to about 500 mg, from about 20 mg to about 300 mg, from about 100 mg to about 200 mg, or from about 100 mg to about 150 mg of the antibody. The time between the first and second doses may be from about a few hours to several weeks. For example, the second time point (i.e., the time when the second dose is administered) can be from about 1 hour to about 7 weeks after the first time point (i.e., the time when the first dose is administered). According to certain exemplary embodiments of the present invention, the second time point can be about 1 hour, about 4 hours, about 6 hours, about 8 hours, about 10 hours, about 12 hours, about 24 hours, about 2 days, about 3 days, about 4 days, about 5 days, about 6 days, about 7 days, about 2 weeks, about 4 weeks, about 6 weeks, about 8 weeks, about 10 weeks, about 12 weeks, about 14 weeks or longer after the first time point. In certain embodiments, the second time point is about 1 week or about 2 weeks. Third and subsequent doses may be similarly administered throughout the course of treatment of the patient.

As used herein, "about" refers to at least 5% more or less of a value. For example, about 100 mg would refer to a range of 95-105 mg.

The invention provides methods of using therapeutic compositions comprising anti-IL-6R antibodies or antigen-binding fragments thereof and, optionally, one or more additional therapeutic agents. The therapeutic compositions of the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the weight of a subject to be administered, target disease, conditions, route of administration, and the like. Various delivery systems are known and can be used to administer the pharmaceutical composition of the invention, e.g., encapsulation in liposomes, microparticles, microcapsules, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The hIL-6R antibody can be administered subcutaneously.

The pharmaceutical composition can also be delivered in a vesicle, in particular a liposome (see Langer (1990) Science 249:1527-1533). In certain situations, the pharmaceutical composition can be delivered in a controlled release system, for example, with the use of a pump or polymeric materials. In another embodiment, a controlled release system can be placed in proximity of the composition's target, thus requiring only a fraction of the systemic dose.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the hIL-6R antibody contained is generally from about 100 to about 200 mg per subcutaneous dosage form.

In accordance with the methods disclosed herein, the anti-hIL-6R antibody (or pharmaceutical formulation comprising the antibody) can be administered to the patient using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer an anti-hIL-6R antibody (or pharmaceutical formulation comprising the antibody). Examples of such devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen and/or autoinjector delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (AbbVie Inc., North Chicago, Ill.), to name only a few.

The use of a microinfusor to deliver an anti-hIL-6R antibody (or pharmaceutical formulation comprising the antibody) to a patient is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., J. Controlled Release 46:107-116 (1996). Microinfusors are particularly useful for the delivery of large doses of therapeutic proteins contained within high concentration (e.g., about 100, 125, 150, 175, 200 or more mg/mL) and/or viscous solutions.

Patient Population

In certain embodiments, the methods and compositions described herein are administered to specific patient populations. These populations include subjects that have a vitreous haze (VH) level greater than or equal to 2 on the Miami 9 step scale. In other embodiments, subjects in this population have a VH level of greater than 3, 4, 5, 6, 7 or 8. According to other embodiments, subjects in this population have a VH level of greater than 4 on the Miami 9 step scale.

In other embodiments, subjects in this population have macular edema. In certain embodiments, a subject with macular edema has a CRT of greater than 300 μm.

In other embodiments, subjects in this population have other signs of intraocular inflammation such as perivascular sheathing of retinal vessels and leakage of retinal vessels.

According to certain embodiments, the methods of the present invention comprise selecting a patient who exhibits any of the aforementioned characteristics, and administering to the patient an anti-IL-6R antibody as described elsewhere herein.

Combination Therapies

The present invention includes methods of treating uveitis and/or macular edema which comprise administering to a patient in need of such treatment an anti-hIL-6R antibody. In certain embodiments, the anti-hIL-6 antibody is administered as a "monotherapy" or single therapeutic agent. In alternative embodiments, the anti-hIL-6 antibody is administered in combination with at least one additional therapeutic agent. Examples of additional therapeutic agents which can be administered in combination with an anti-hIL-6R antibody in the practice of the methods of the present invention include, but are not limited to, corticosteroids, and any other compound known to treat, prevent, or ameliorate uveitis and/or macular edema in a human subject. Specific, non-limiting examples of additional therapeutic agents that may be administered in combination with an anti-hIL-6R antibody in the context of a method of the present invention include, but are not limited to methotrexate, and prednisone. In the present methods, the additional therapeutic agent(s) can be administered concurrently or sequentially with the anti-hIL-6R antibody. For example, for concurrent administration, a pharmaceutical formulation can be made which contains both an anti-hIL-6R antibody and at least one additional therapeutic agent. The amount of the additional therapeutic agent that is administered in combination with the anti-hIL-6R antibody in the practice of the methods of the present invention can be easily determined using routine methods known and readily available in the art.

The disclosure of the invention provides for pharmaceutical compositions comprising any of the following:

A composition comprising from 100 to 200 mg of sarilumab (SAR153191) to be administered every two weeks and from 15 to 80 mg of prednisone to be administered every day.

A composition comprising about 200 mg of sarilumab (SAR153191) to be administered every two weeks and from 15 to 80 mg of prednisone to be administered every day.

A composition comprising from 100 to 150 mg of sarilumab (SAR153191) administered every two weeks, from 15 to 80 mg of prednisone to be administered every day and from 6 to 25 mg of methotrexate to be administered every week.

A composition comprising from 100 to 200 mg of sarilumab (SAR153191) administered every two weeks, from 15 to 80 mg of prednisone to be administered every day and from 6 to 25 mg of methotrexate to be administered every week.

The disclosure of the invention provides for methods of improving symptoms associated with uveitis comprising any of the following:

A method comprising administering from 100 to 200 mg of sarilumab (SAR153191) every two weeks and from 15 to 80 mg per day of to a subject in need thereof.

A method comprising administering about 200 mg of sarilumab (SAR153191) every two weeks and from 15 to 80 mg per day of prednisone to a subject in need thereof.

Examples

Example 1. Anti-IL6R Antibody is Effective in Treatment of Uveitis and/or Macular Edema in Humans A study was performed to evaluate the efficacy and safety of sarilumab administered subcutaneously every 2 weeks (q2w) in patients with non-infectious, intermediate, posterior or pan-uveitis.

This was a randomized, double-masked, placebo-controlled, parallel group study. The randomization was 2:1 (sarilumab:placebo) and patients were stratified according to screening vitreous haze (VH) level (VH=4 versus VH<4), macular edema (Yes, No), and uveitis etiology (systemic and idiopathic).

The primary objectives were to evaluate: the efficacy of 200 mg sarilumab q2w at Week 16 in patients with non-infectious uveitis (NIU); the change in best corrected visual acuity (BCVA); the safety of subcutaneous sarilumab in patients with NIU; the change in macular edema; the change in other signs of ocular inflammation; the effect on retinal vessel leakage; the effect of sarilumab on reducing concomitant immuno-suppressant therapy at Week 16; the change in ocular inflammation in the anterior chamber; the pharmacokinetics (PK) of sarilumab in NIU patients; and the immunogenicity anti-drug antibody (ADA). Also evaluated were the effect on serum biomarkers of inflammation such as high sensitivity C-reactive protein (hs-CRP) and serum amyloid A (SAA); the effect on underlying systemic disease when appropriate; the effect of sarilumab on ocular disease at Week 52; the effect of sarilumab on reducing concomitant immuno-suppressant therapy at Week 52; and the characteristics of uveitis when symptoms worsen.

The study included 2 periods:

Principal treatment period (part A): At inclusion, the patient had to be already under treatment with prednisone or equivalent steroid (as single therapy or in combination with methotrexate); sarilumab or placebo was added to the ongoing therapy. After 2 study treatment injections (Visit 4), if improvement was confirmed on at least 2 consecutive evaluations, a tapering of the background therapy was started following pre-specified rules. Clinical (efficacy and safety) evaluations were performed every other week, for 16 weeks.

Extension treatment period (part B): If the patient completed part A and was defined as a responder, he or she continued with the same double-masked treatment until completion of 1 year (last injection at Week 50). Clinical (efficacy and safety) evaluations were performed every 4 weeks.

In addition, there were 2 further options:

Open-label treatment periods (part C): At any time during part A, patients experiencing worsening symptoms, or those defined as non-responders at Week 16, were eligible at the discretion of the Investigator- and in participating countries where this procedure had been accepted- to continue treatment with open-label sarilumab in part C. Patients were treated for up to 34 extra weeks (up to 18 extra injections). Efficacy and safety evaluations were performed.

An optional Genomics sub-study for banking DNA and RNA for exploratory research was proposed to the patients. Approximately 57 patients (assumptions of power of 80% for comparison of 59% response expected in sarilumab and 20% response expected in placebo) were planned to be randomized.

Patients with non-infectious intermediate-, posterior-, or pan-uveitis with active disease or recently active (activity in the previous 3 months) disease. Patients were to be receiving corticosteroid as single immunosuppressive therapy or in combination with Methotrexate. No other immunosuppressive therapy was permitted. Patients must have been receiving oral prednisone (15 mg and <80 mg/day [or equivalent oral corticosteroid]) as a single immunosuppressive therapy or in combination with methotrexate (MTX) 25 mg/week) orally, or equivalent intravenous, intramuscular, or subcutaneous.

Primary endpoint was the proportion of patients at Week 16 with (1) at least a 2-step reduction in adjudicated VH (Miami 9-point scale) in the study eye, or (2) a dose of prednisone or equivalent oral corticosteroid <10 mg/day at Week 16. Other efficacy endpoints at Week 16 included the change in baseline in Central retinal thickness (CRT), Best-corrected visual acuity, Corticosteroid dosage, Retinal vessel leakage (FA) (Exploratory), and Clinical Assessment Score (Exploratory).

Study Patients

A total of 58 patients were randomized: 38 patients in the sarilumab group and 20 patients in the placebo group. All 58 patients were exposed to IMP (investigational medicinal product) and included in the mITT (modified intent-to-treat) population. For sake of clarity, mITT population includes all randomized patients who received at least one IMP injection. A total of 28 (73.7%) patients in the sarilumab group and 13 (65.0%) in the placebo group completed the principal treatment period (part A); one patient in the placebo group was not included in the completer population owing to a non-evaluable primary efficacy endpoint (VH assessment) at week 16.

Demographics and patient characteristics at baseline were well-balanced between the treatment groups (Table 1). Of note, the number of patients with macular edema (defined as a CRT=300 μm) was lower in the sarilumab group compared to the placebo group (21 [55.3%] vs 13 [65.0%], respectively).

TABLE 1

Description of stratification factors (as documented in IVRS database) - Randomized population VH level stratum is based on adjudicated value at screening

|  | Placebo (N = 20) | SAR153191 200 mg q2w (N = 38) | All (N = 58) |
|---|---|---|---|
| Vitreous Haze level (J Davis/Miami 9-step scale) [n(%)] | | | |
| Number | 20 | 38 | 58 |
| VH <4 | 17 (85.0%) | 32 (84.2%) | 49 (84.5%) |
| VH >=4 | 3 (15.0%) | 6 (15.8%) | 9 (15.5%) |
| Uveitis etiology [n(%)] | | | |
| Number | 20 | 38 | 58 |
| Idiopathic | 13 (65.0%) | 25 (65.8%) | 38 (65.5%) |
| Systemic | 7 (35.0%) | 13 (34.2%) | 20 (34.5%) |
| Macular edema [n(%)] | | | |
| Number | 20 | 38 | 58 |
| Yes | 13 (65.0%) | 21 (55.3%) | 34 (58.6%) |
| No | 7 (35.0%) | 17 (44.7%) | 24 (41.4%) |

Macular edema stratum is based on median of adjudicated CRT value automatically measured by the device software at screening.

The median corticosteroid dose at baseline was 20 mg/day. Of 58 patients, one (1.7%) had a corticosteroid dose at baseline of less than 15 mg/day, 45 (77.6%) had a corticosteroid dose at baseline of 15 or 20 mg/day, 12 (20.7%) had a corticosteroid dose at baseline of 20 or 40 mg/day, and 0 patients had a corticosteroid dose at baseline of greater than 40 mg/day. Furthermore, the majority, 55 (94.8%) patients had active disease at baseline and in 29 (50%) patients this was pan-uveitis.

The median time from first diagnosis was 17.92 months (1.49 years) and it was higher in the placebo group (24.02 months) when compared with the sarilumab group (17.58 months).

At baseline, the number of patients with adjudicated VH<4 was higher in the sarilumab group (49 patients [86.0%]) when compared to the placebo group (17 patients [85.0%]). The median adjudicated CRT at baseline was lower in the sarilumab group (298.0 μm) compared to the placebo group (308.0 μm). Also the percentage of patients with macular edema (defined as a CRT 300 μm) was lower in the sarilumab group compared to the placebo group (i.e., 18 patients [48.6%] for sarilumab group versus 14 patients [70.0%] for the placebo group, respectively). See Table 2.

TABLE 2

Adjudicated ocular assessment at baseline for study eye - Randomized population

|  | Placebo (N = 20) | SAR153191 200 mg q2w (N = 38) | All (N = 58) |
|---|---|---|---|
| Vitreous Haze (J Davis/Miami 9-step scale) | | | |
| Number | 20 | 37 | 57 |
| 0 | 6 (30.0%) | 13 (35.1%) | 19 (33.3%) |
| 1 | 9 (45.0%) | 14 (37.8%) | 23 (40.4%) |
| 2 | 2 (10.0%) | 2 (5.4%) | 4 (7.0%) |
| 3 | 0 | 3 (8.1%) | 3 (5.3%) |
| 4 | 1 (5.0%) | 2 (5.4%) | 3 (5.3%) |
| 5 | 1 (5.0%) | 2 (5.4%) | 3 (5.3%) |
| 6 | 0 | 1 (2.7%) | 1 (1.8%) |
| 7 | 0 | 0 | 0 |
| 8 | 1 (5.0%) | 0 | 1 (1.8%) |
| VH < 4 | 17 (85.0%) | 32 (86.5%) | 49 (86.0%) |
| VH ≥ 4 | 3 (15.0%) | 5 (13.5%) | 8 (14.0%) |
| Vitreous Haze (J Davis/Miami 7-step scale) | | | |
| Number | 20 | 37 | 57 |
| 0 | 6 (30.0%) | 13 (35.1%) | 19 (33.3%) |
| 1 | 9 (45.0%) | 14 (37.8%) | 23 (40.4%) |
| 2 | 2 (10.0%) | 5 (13.5%) | 7 (12.3%) |
| 3 | 1 (5.0%) | 2 (5.4%) | 3 (5.3%) |
| 4 | 1 (5.0%) | 2 (5.4%) | 3 (5.3%) |
| 5 | 0 | 1 (2.7%) | 1 (1.8%) |
| 6 | 1 (5.0%) | 0 | 1 (1.8%) |
| VH < 3 | 17 (85.0%) | 32 (86.5%) | 49 (86.0%) |
| VH ≥ 3 | 3 (15.0%) | 5 (13.5%) | 8 (14.0%) |
| Central Retinal Thickness (Automatic measurement from SD-OCT) (μm) | | | |
| Number | 20 | 37 | 57 |
| Mean (SD) | 308.9 (53.1) | 341.6 (149.6) | 330.2 (124.9) |
| Median | 308.0 | 298.0 | 303.0 |
| Q1:Q3 | 271.0:338.0 | 273.0:340.0 | 273.0:339.0 |
| Min:Max | 223:432 | 148:992 | 148:992 |
| CRT < 300 | 6 (30.0%) | 19 (51.4%) | 25 (43.9%) |
| CRT ≥ 300 | 14 (70.0%) | 18 (48.6%) | 32 (56.1%) |
| Central Retinal Thickness (CRT) (Manual measurement) (μm) | | | |
| Number | 20 | 37 | 57 |
| Mean (SD) | 217.2 (64.8) | 248.4 (165.1) | 237.4 (138.5) |
| Median | 195.3 | 194.0 | 194.0 |
| Q1:Q3 | 170.5:255.8 | 173.5:226.0 | 171.5:248.5 |
| Min:Max | 125:380 | 94:927 | 94:927 |
| CRT < 300 | 18 (90.0%) | 30 (81.1%) | 48 (84.2%) |
| CRT ≥ 300 | 2 (10.0%) | 7 (18.9%) | 9 (15.8%) |

(SD: Standard Deviation)

Investigator's ocular assessments of VH<4 and VH<3 at baseline are described in the following Table 3. A total of 14 (24.1%) patients had VH=4; 9 patients ([23.7%]) were identified in the sarilumab group, and 5 patient ([25.0%]) were identified in the placebo group). The number of patients with BCVA=70 letters at baseline was lower in the sarilumab group compared to the placebo group (i.e., 23 patients [60.5%] in the sarilumab group versus 16 patients [80.0%] in the placebo group, respectively). A majority of the patients (55 patients; 94.8%) presented with an abnormal fluorescein angiography (FA) at baseline. See Table 3.

TABLE 3

Investigator's ocular assessment at baseline for study eye - Randomized population

|  | Placebo (N = 20) | SAR153191 200 mg q2w (N = 38) | All (N = 58) |
|---|---|---|---|
| Vitreous Haze (J Davis/Miami 9-step scale) | | | |
| Number | 20 | 38 | 58 |
| 0 | 4 (20.0%) | 7 (18.4%) | 11 (19.0%) |
| 1 | 3 (15.0%) | 10 (26.3%) | 13 (22.4%) |
| 2 | 5 (25.0%) | 6 (15.8%) | 11 (19.0%) |
| 3 | 3 (15.0%) | 6 (15.8%) | 9 (15.5%) |
| 4 | 3 (15.0%) | 5 (13.2%) | 8 (13.8%) |
| 5 | 2 (10.0%) | 1 (2.6%) | 3 (5.2%) |
| 6 | 0 | 2 (5.3%) | 2 (3.4%) |
| 7 | 0 | 1 (2.6%) | 1 (1.7%) |
| 8 | 0 | 0 | 0 |
| VH < 4 | 15 (75.0%) | 29 (76.3%) | 44 (75.9%) |
| VH ≥ 4 | 5 (25.0%) | 9 (23.7%) | 14 (24.1%) |
| Vitreous Haze (J Davis/Miami 7-step scale) | | | |
| Number | 20 | 38 | 58 |
| 0 | 4 (20.0%) | 7 (18.4%) | 11 (19.0%) |
| 1 | 3 (15.0%) | 10 (26.3%) | 13 (22.4%) |
| 2 | 8 (40.0%) | 12 (31.6%) | 20 (34.5%) |
| 3 | 3 (15.0%) | 5 (13.2%) | 8 (13.8%) |
| 4 | 2 (10.0%) | 1 (2.6%) | 3 (5.2%) |
| 5 | 0 | 3 (7.9%) | 3 (5.2%) |
| 6 | 0 | 0 | 0 |
| VH < 3 | 15 (75.0%) | 29 (76.3%) | 44 (75.9%) |
| VH ≥ 3 | 5 (25.0%) | 9 (23.7%) | 14 (24.1%) |

TABLE 3-continued

Investigator's ocular assessment at baseline
for study eye - Randomized population

|  | Placebo (N = 20) | SAR153191 200 mg q2w (N = 38) | All (N = 58) |
|---|---|---|---|
| Central Retinal Thickness (CRT) measured by SD-OCT (μm) | | | |
| Number | 20 | 38 | 58 |
| Mean (SD) | 302.3 (60.1) | 329.8 (154.1) | 320.3 (129.6) |
| Median | 299.5 | 288.0 | 296.5 |
| Q1:Q3 | 262.5:333.5 | 254.0:337.0 | 255.0:335.0 |
| Min:Max | 205:432 | 153:1048 | 153:1048 |
| CRT < 300 | 10 (50.0%) | 21 (55.3%) | 31 (53.4%) |
| CRT ≥ 300 | 10 (50.0%) | 17 (44.7%) | 27 (46.6%) |
| Best Corrected Visual Acuity (ETDRS letters score) | | | |
| Number | 20 | 38 | 58 |
| Mean (SD) | 74.5 (13.4) | 70.4 (14.6) | 71.8 (14.2) |
| Median | 79.0 | 73.5 | 75.0 |
| Q1:Q3 | 74.0:83.0 | 63.0:80.0 | 64.0:81.0 |
| Min:Max | 35:88 | 24:93 | 24:93 |
| BCVA < 70 letters | 4 (20.0%) | 15 (39.5%) | 19 (32.8%) |
| BCVA ≥ 70 letters | 16 (80.0%) | 23 (60.5%) | 39 (67.2%) |
| Fluorescein Angiography (FA) | | | |
| Number | 20 | 38 | 58 |
| Normal | 1 (5.0%) | 2 (5.3%) | 3 (5.2%) |
| Abnormal | 19 (95.0%) | 36 (94.7%) | 55 (94.8%) |
| Anterior Chamber (Cells) | | | |
| Number | 20 | 38 | 58 |
| 0 | 15 (75.0%) | 28 (73.7%) | 43 (74.1%) |
| +0.5 | 3 (15.0%) | 4 (10.5%) | 7 (12.1%) |
| +1 | 2 (10.0%) | 5 (13.2%) | 7 (12.1%) |
| +2 | 0 | 1 (2.6%) | 1 (1.7%) |
| +3 | 0 | 0 | 0 |
| Iris/Pupil Pathology (Flare) | | | |
| Number | 20 | 38 | 58 |
| Normal | 16 (80.0%) | 33 (86.8%) | 49 (84.5%) |
| Abnormal | 4 (20.0%) | 5 (13.2%) | 9 (15.5%) |
| Vitreous (cells) | | | |
| Number | 20 | 38 | 58 |
| 0 | 2 (10.0%) | 7 (18.4%) | 9 (15.5%) |
| +0.5 | 3 (15.0%) | 7 (18.4%) | 10 (17.2%) |
| +1 | 7 (35.0%) | 14 (36.8%) | 21 (36.2%) |
| +2 | 8 (40.0%) | 8 (21.1%) | 16 (27.6%) |
| +3 | 0 | 2 (5.3%) | 2 (3.4%) |
| Intraocular Pressure (IOP) in mmHg | | | |
| Number | 20 | 38 | 58 |
| Mean (SD) | 16.3 (4.3) | 15.0 (3.4) | 15.4 (3.7) |
| Median | 16.5 | 15.0 | 16.0 |
| Q1:Q3 | 13.0:18.5 | 13.0:17.0 | 13.0:18.0 |
| Min:Max | 9:26 | 8:24 | 8:26 |
| Lid erythema | | | |
| Number | 20 | 38 | 58 |
| 0 | 20 (100%) | 38 (100%) | 58 (100%) |
| +0.5 | 0 | 0 | 0 |
| +1 | 0 | 0 | 0 |
| +2 | 0 | 0 | 0 |
| +3 | 0 | 0 | 0 |
| Lid edema | | | |
| Number | 20 | 38 | 58 |
| 0 | 20 (100%) | 38 (100%) | 58 (100%) |
| +0.5 | 0 | 0 | 0 |
| +1 | 0 | 0 | 0 |
| +2 | 0 | 0 | 0 |
| +3 | 0 | 0 | 0 |
| Conjunctival hyperemia | | | |
| Number | 20 | 38 | 58 |
| 0 | 20 (100%) | 37 (97.4%) | 57 (98.3%) |
| +0.5 | 0 | 0 | 0 |
| +1 | 0 | 1 (2.6%) | 1 (1.7%) |
| +2 | 0 | 0 | 0 |
| +3 | 0 | 0 | 0 |
| Conjunctival edema | | | |
| Number | 20 | 38 | 58 |
| 0 | 20 (100%) | 38 (100%) | 58 (100%) |
| +0.5 | 0 | 0 | 0 |
| +1 | 0 | 0 | 0 |
| +2 | 0 | 0 | 0 |
| +3 | 0 | 0 | 0 |
| Subconjunctival hemorrhage | | | |
| Number | 20 | 38 | 58 |
| 0 | 20 (100%) | 37 (97.4%) | 57 (98.3%) |
| +0.5 | 0 | 0 | 0 |
| +1 | 0 | 1 (2.6%) | 1 (1.7%) |
| +2 | 0 | 0 | 0 |
| +3 | 0 | 0 | 0 |
| Corneal edema | | | |
| Number | 20 | 38 | 58 |
| 0 | 20 (100%) | 38 (100%) | 58 (100%) |
| +0.5 | 0 | 0 | 0 |
| +1 | 0 | 0 | 0 |
| +2 | 0 | 0 | 0 |
| +3 | 0 | 0 | 0 |
| Corneal staining/erosion | | | |
| Number | 20 | 38 | 58 |
| 0 | 20 (100%) | 38 (100%) | 58 (100%) |
| +0.5 | 0 | 0 | 0 |
| +1 | 0 | 0 | 0 |
| +2 | 0 | 0 | 0 |
| +3 | 0 | 0 | 0 |
| Anterior chamber flare | | | |
| Number | 20 | 36 | 56 |
| 0 | 15 (75.0%) | 30 (83.3%) | 45 (80.4%) |
| +0.5 | 0 | 0 | 0 |
| +1 | 2 (10.0%) | 6 (16.7%) | 8 (14.3%) |
| +2 | 3 (15.0%) | 0 | 3 (5.4%) |
| +3 | 0 | 0 | 0 |
| +4 | 0 | 0 | 0 |
| Lens status | | | |
| Number | 20 | 38 | 58 |
| Phakic | 17 (85.0%) | 29 (76.3%) | 46 (79.3%) |
| Pseudophakic | 3 (15.0%) | 9 (23.7%) | 12 (20.7%) |
| Aphakic | 0 | 0 | 0 |
| Lens opacities for phakic eyes | | | |
| Number | 17 | 29 | 46 |
| 1 | 12 (70.6%) | 25 (86.2%) | 37 (80.4%) |
| 2 | 5 (29.4%) | 4 (13.8%) | 9 (19.6%) |
| 3 | 0 | 0 | 0 |
| Optic nerve, (Cup/Disk ratio) | | | |
| Number | 20 | 38 | 58 |
| Mean (SD) | 0.190 (0.121) | 0.208 (0.142) | 0.202 (0.134) |

TABLE 3-continued

Investigator's ocular assessment at baseline
for study eye - Randomized population

|  | Placebo (N = 20) | SAR153191 200 mg q2w (N = 38) | All (N = 58) |
|---|---|---|---|
| Median | 0.200 | 0.200 | 0.200 |
| Q1:Q3 | 0.100:0.300 | 0.100:0.300 | 0.100:0.300 |
| Min:Max | 0.00:0.30 | 0.00:0.80 | 0.00:0.80 |

9-step scale is changed to a 7-step scale by combining slides 2 and 3 as a single step and slides 6 and 7 as a single step per FDA recommendations Of note, disagreements have been observed between the investigator's assessments and adjudicated assessments on VH. The adjudicated assessment for VH was less severe than the investigator assessment in over 52.6% of the patient population. Furthermore there were a percentage of patients that have two steps or more of difference between both evaluations. Therefore, an additional sensitivity analysis for the primary endpoint using VH values per Investigator has been included. No differences between the investigator's assessments and adjudicated assessments on CRT were observed in 55.2% of the patients and the adjudicated assessment for CRT was less severe than the Investigator assessment in 12 (20.7%) patients.

Dosage and Duration

Exposure to injections was equivalent in both groups with a mean of 14.1 weeks of IMP injection exposure during the 16 weeks of Part A. The overall compliance was also equivalent in both groups; all 58 patients received at least 80% of the theoretical dose.

Efficacy

Primary Efficacy Endpoint

The primary endpoint (proportion of patients with a 2-step reduction in VH or corticosteroids dose <10 mg/day at week 16) analysis is based on the adjudicated VH value. Results of the primary endpoint analysis are presented in Table 4.

The proportion of patients with 2-step reduction in VH or corticosteroids dose <10 mg/day was higher in the sarilumab group (46.1%) when compared with placebo (30.0%), however the difference was not statistically significant (p=0.2354).

The primary efficacy endpoint was chosen to assess the efficacy of sarilumab in reducing the ocular inflammation associated with uveitis. It was expected to include patients with important VH score, for whom the reduction of VH value was essential. Finally, the recruited population presented less severe VH values, because patients with severe VH are treated with concomitant immunosuppressant medications which were not allowed in this study.

Additional endpoints (such as BCVA) were aimed at the evaluation of the efficacy of sarilumab on functional parameters.

The comparison of the proportions of responders between the 2 treatment groups was performed for each complete datasets using Cochran-Mantel-Haenszel (CMH) test at 2-sided alpha level of 0.10.

TABLE 4

Primary efficacy analysis - mITT population

|  | Placebo (N = 20) | SAR153191 200 mg q2w (N = 38) |
|---|---|---|
| Patients with decrease in VH ≥ 2 or corticosteroids dose < 10 mg/day at week 16 |  |  |
| Combined estimate for proportion of responders (%) | 30.0 | 46.1 |
| Comparison vs placebo |  |  |
| Combined estimate for odds ratio |  | 2.1 |
| 90% CI |  | (0.8 to 5.6) |
| p-value |  | 0.2354 |

Note:

Multiple imputation method is used to address missing values in the mITT population (seeds = 13480, 26960; number of imputations = 100).

Combined estimate for proportion of responders is obtained by averaging out all the proportion of responders of the different imputed data sets. Combined estimate for odds ratio is obtained by combining the log-transformation of odds ratio from CMH analyses of the different imputed datasets, using Rubin's formulae, and then by back-transforming the combined estimate.

The CMH analyses are adjusted for randomization stratification factor VH level (VH >= 4 versus VH < 4).

Responder status is defined using adjudicated VH and corticosteroid values on time windowed week 16.

TABLE 5

Primary efficacy endpoint components according to responder status - mITT population

|  | Placebo (N= 20) | SAR153191 200 mg q2w (N = 38) |
|---|---|---|
| Responders | 6 (30.0%) | 17 (44.7%) |
| Decrease in VH ≥ 2 at week 16 | 2 (10.0%) | 6 (15.8%) |
| Corticosteroids dose < 10 mg/day at week 16 | 5 (25.0%) | 16 (42.1%) |
| Non-responders | 13 (65.0%) | 20 (52.6%) |
| Did not complete the principal treatment period (part A) due to lack of efficacy | 6 (30.0%) | 6 (15.8%) |
| No decrease in VH ≥ 2 and corticosteroids dose ≥10 mg/day at week 16 | 6 (30.0%) | 11 (28.9%) |
| No decrease in VH ≥ 2 and corticosteroids dose missing at week 16 | 0 | 3 (7.9%) |
| Non-responder according to medical review | 1 (5.0%) | 0 |

VH values are adjudicated VH values at time windowed week 16.
Corticosteroid values are based on time windowed week 16.

Results of the sensitivity analysis of 2-step reduction in VH or corticosteroids dose <10 mg/day considering missing responder status as non-responder was similar to the primary analysis (See Table 6).

Components for the proportion of patients with 2-step or greater reduction in VH or a dose of prednisone or equivalent oral corticosteroid <10 mg/day at Week 16 considering missing responder as non-responder were also calculated.

TABLE 6

Sensitivity analysis: proportion of patients with at least 2-step reduction inadjudicated VH or a dose of prednisone or equivalent oral corticosteroid <10 mg/day at Week 16 considering missing responder status as non-responder - mITT

| | Placebo (N = 20) | SAR153191 200 mg q2w (N = 38) |
|---|---|---|
| Patients with decrease in VH ≥ 2 or corticosteroids dose < 10 mg/day at Week 16 | | |
| Responders [n(%)] | 6 (30.0%) | 17 (44.7%) |
| Comparison vs placebo | | |
| Common odds ratio | | 2 |
| 90% exact CI | | (0.6 to 6.2) |
| Exact p-value | | 0.3893 |

Note:
Common odds ratio comes from CMH analysis adjusted for randomization stratification factor VH level (VH >= 4 versus VH < 4). Two-sided confidence interval (CI) and p-value from exact stratified test (Gart 1971).
Responder status is defined using adjudicated VH and corticosteroid values on time windowed Week 16.
Patients with missing responder status at Week 16 are considered as non-responders.

Other Key Efficacy Endpoints

As per investigator assessment, the proportion of patients with a 2-step reduction in VH or corticosteroids dose <10 mg/day was nominally significantly higher (p=0.0372) in the sarilumab group (64.0%) compared with placebo (35.0%). See Table 7. Components for the proportion of patients with 2-step or greater reduction in VH or a dose of prednisone or equivalent oral corticosteroid <10 mg/day at Week 16 based on Investigator read values were also calculated. See Table 8.

TABLE 7

Sensitivity analysis: proportion of patients with 2-step or greater reduction in VH based on investigator or a dose of prednisone or equivalent oral corticosteroid < 10 mg/day at week 16 - mITT population

| | Placebo (N = 20) | SAR153191 200 mg q2w (N = 38) |
|---|---|---|
| Patients with decrease in VH ≥ 2 or corticosteroids dose < 10 mg/day at week 16 | | |
| Combined estimate for proportion of responders (%) | 35.0 | 64.0 |
| Comparison vs placebo | | |
| Combined estimate for odds ratio | | 3.7 |
| 90% CI | | (1.3 to 10.4) |
| 95% CI | | (1.1 to 12.6) |
| p-value | | 0.0372 |

Note:
Multiple imputation method is used to address missing values in the mITT population (seeds = 13480, 26960; number of imputations = 100).
Combined estimate for proportion of responders is obtained by averaging out all the proportion of responders of the different imputed data sets. Combined estimate for odds ratio is obtained by combining the log-transformation of odds ratio from CMH analyses of the different imputed datasets, using Rubin's formulae, and then by back-transforming the combined estimate.
The CMH analyses are adjusted for randomization stratification factor VH level (VH >= 4 versus VH < 4).
Responder status is defined using VH based on investigator assessment and corticosteroid values on time windowed week 16.

TABLE 8

Sensitivity analysis components of proportion of patients with 2-step or greater reduction in VH based on investigator or a dose of prednisone or equivalent oral corticosteroid <10 mg/day at week 16 - mITT population

| | Placebo (N = 20) | SAR153191 200 mg q2w (N = 38) |
|---|---|---|
| Responders | 7 (35.0%) | 23 (60.5%) |
| Decrease in VH ≥ 2 at week 16 | 4 (20.0%) | 16 (42.1%) |
| Corticosteroids dose < 10 mg/day at week 16 | 5 (25.0%) | 16 (42.1%) |
| Non-responders | 13 (65.0%) | 13 (34.2%) |
| Did not complete the principal treatment period (part A) due to lack of efficacy | 6 (30.0%) | 6 (15.8%) |
| No decrease in VH ≥ 2 and corticosteroids dose ≥ 10 mg/day at week 16 | 6 (30.0%) | 5 (13.2%) |
| No decrease in VH ≥ 2 and corticosteroids dose missing at week 16 | 0 | 2 (5.3%) |
| Non-responder according to medical review | 1 (5.0%) | 0 |

VH values are based on investigator assessment at time windowed week 16.
Corticosteroid values are based on time windowed week 16.

Key Secondary Efficacy Endpoints
Change from Baseline in Adjudicated VH

A statistically significant difference for the change in adjudicated VH from baseline was observed between the sarilumab and placebo treatment groups. The LS mean change in adjudicated VH from baseline to week 16 was higher in the sarilumab group (−0.87) compared to the placebo group (−0.13) with an LS mean difference vs. placebo of −0.74 (90% CI: −1.223 to −0.262); p=0.0127. See Table 9.

TABLE 9

Secondary efficacy endpoint - Change from baseline in adjudicated VH - mITT population

| Vitreous Haze (J Davis/Miami 9-step scale) | Placebo (N = 20) | SAR153191 200 mg q2w (N = 38) |
|---|---|---|
| Baseline | | |
| Number | 20 | 38 |
| Mean (SD) | 1.7 (2.0) | 1.4 (1.6) |
| Median | 1.0 | 1.0 |
| Min:Max | 0:7 | 0:7 |
| Week 16 | | |
| Number | 13 | 28 |
| Mean (SD) | 1.4 (1.6) | 0.7 (0.9) |
| Median | 1.0 | 0.0 |
| Min:Max | 0:6 | 0:4 |
| Change from Baseline | | |
| Number | 13 | 28 |
| Mean (SD) | −0.1 (1.5) | −0.9 (1.4) |
| Median | 0.0 | −1.0 |
| Min:Max | −4:1 | −5:1 |
| LS Mean (SE)$^a$ | −0.1 (0.23) | −0.9 (0.16) |
| 90% CI | (−0.519 to 0.267) | (−1.146 to −0.592) |
| LS Mean difference (SE) vs. placebo$^a$ | | −0.7 (0.29) |
| 90% CI | | (−1.223 to −0.262) |
| 95% CI | | (−1.319 to −0.166) |
| p-value | | 0.0127 |

CI: confidence interval;
MMRM: Mixed model for repeated measurements;
LS mean: least square mean calculated using mixed model
Note:
only patients who had adjudicated VH assessed at baseline and post-baseline are included in Change from Baseline analysis.
$^a$MMRM model with treatment groups, visits and visit-by-treatment groups interaction as fixed categorical effects, as well as, fixed continuous covariate of baseline adjudicated VH
An unstructured correlation matrix is used to model the within-patient errors.

Vitreous Haze Preliminary Conclusions

Only 7 patients in this population presented at baseline with VH>=4. In general, the severe patients were harder to recruit in this study since the standard of care of patients with severe disease includes several concomitant immunosuppressive therapies which were prohibited in this study. In addition, disagreements in the assessment of VH from pre-treatment evaluations between the investigator and adjudicator were noted. At week 16, the proportion of patients with a 2-step reduction in VH per Investigator assessment or corticosteroids dose <10 mg/day was statistically significantly higher in the sarilumab group (64.0%) when compared with placebo (35.0%) (OR: 3.7 (90% CI: 1.3 to 10.4, p=0.0372). In addition changes in VH per adjudicated assessment was statistically significantly greater when compared to the placebo group) (LS mean difference vs. placebo of −0.74 (90% CI: −1.223 to −0.262, p=0.0127).

Prednisone or Oral Corticosteroid Dose

At week 12, following 5 injections of sarilumab, a notable difference in the oral corticosteroid dose when compared with the placebo group was observed.

The LS mean change in prednisone or oral corticosteroid dose, from baseline to week 16 was higher in the sarilumab group (−11.20 mg/day) compared to the placebo group (−7.85 mg/day), but with no statistically significant difference.

Adjudicated Central Retinal Thickness

The LS mean change in adjudicated CRT from baseline to Week 16 was decreased to a greater extent in the sarilumab group (−35.4 μm) when compared to the placebo group (−8.9 μm) with an LS mean difference versus placebo of −26.5 (90% CI: −50.41 to −2.68) (p=0.0683). Since 8 patients in the study presented with very high baseline CRT values that had a greater capacity to show an improvement (Table 10), MMRM model planned in the SAP on the mITT population was not appropriate to fit the change in adjudicated CRT (as confirmed by the studentized residuals plots). An analysis evaluating the change from baseline in adjudicated CRT in the mITT population excluding patients with high baseline CRT was also performed and detailed in Table 10. Excluding patients with high baseline CRT, the LS mean change in adjudicated CRT from baseline to week 16 was decreased in the sarilumab group (−5.27 μm) and was increased in the placebo group (1.79 μm) with an LS mean difference vs. placebo of −7.06 (90% CI: −22.022 to 7.904) (p=0.4328). The LS mean change in adjudicated CRT from baseline to Week 16 was decreased in the sarilumab group (−6.4%) when compared to no change in the placebo group with an LS mean difference versus placebo of −6.4% (90% CI: −12.374 to −0.350) (p=0.0825) (Table 10).

TABLE 10

Change from baseline in adjudicated CRT - mITT population excluding patients with high baseline CRT

| Central Retinal Thickness (CRT) (Automatic measurement from SD-OCT) (μm) | Placebo (N = 20) | SAR153191 200 mg q38 |
|---|---|---|
| Baseline | | |
| Number | 20 | 38 |
| Mean (SD) | 306.1 (58.9) | 338.4 (155.5) |
| Median | 306.5 | 293.0 |
| Min:Max | 214:432 | 153:1048 |
| Week 16 | | |
| Number | 14 | 24 |
| Mean (SD) | 299.2 (60.4) | 292.7 |
| Median | 294.5 | 291.00 |
| Min:Max | 211:429 | 153:576 |
| Change from | | |
| Number | 14 | 24 |
| Mean (SD) | 1.54 (14.36) | −7.27 (17.97 |
| Median | −1.72 | −4.15 |
| Min:Max | −12.0:41.6 | −48.3:21.9 |
| LS Mean (SE) <sup>a</sup> | 0.0 (2.90) | −6.4 (2.15) |
| 90% CI | (−4.923 to 4.934) | (−10.008 to −2.705) |
| LS Mean difference (SE) vs. placebo <sup>a</sup> | | −6.4 (3.55) |
| 90% CI | | (−12.374 to −0.350) |
| p-value | | 0.0825 |

CI: confidence interval;
MMRM: Mixed model for repeated measurements;
LS mean: least square mean calculated using mixed model
Note:
only patients who had adjudicated CRT (Automatic measurement from SD-OCT) assessed at baseline and post-baseline are included.
<sup>a</sup> MMRM model with treatment groups, randomization strata of VH level (<4, >=4), visits and visit-by-treatment groups interaction as fixed categorical effects, as well as, fixed continuous covariate of baseline CRT (Automatic measurement from SD-OCT)
An unstructured correlation matrix is used to model the within-patient errors.
Within group LS means and standard errors (SE) are calculated using weights equal to the observed proportion of patients in strata variable levels: VH level (<4, >=4) in the study population
High baseline CRT is defined as baseline CRT >= 432 based on the review of baseline CRT distribution Best Corrected Visual Acuity The BCVA remains the most clinical relevant functional parameter in the treatment of uveitis. Other important variables (VH, CRT, FA findings) remain critical inflammatory markers for the demonstration the efficacy of new treatments. At week 10, following 4 injections of sarilumab, statistically significant improvements in BCVA were observed (Table 11).

A statistically significant difference in the change in BCVA from baseline to week 16 was observed. The LS mean change in BCVA from baseline to week 16 was significantly higher in the sarilumab group (8.51) compared to the placebo group (3.87) with an LS mean difference vs. placebo of 4.65 (90% CI: 1.091 to 8.201); p=0.0333. The mean improvement in the sarilumab group was 8.93 letters (almost 2 lines on the ETDRS chart) compared with 3.60 letters in the placebo group.

TABLE 11

Secondary efficacy endpoint - Change from baseline in BCVA- mITT population

| Best Corrected Visual Acuity (ETDRS letters score) | Placebo (N = 20) | SAR153191 200 mg q2w (N = 38) |
|---|---|---|
| Baseline | | |
| Number | 20 | 38 |
| Mean (SD) | 74.50 (13.4) | 70.37 (14.6) |
| Median | 79.0 | 73.5 |
| Min:Max | 35:88 | 24:93 |
| Week 16 | | |
| Number | 15 | 29 |
| Mean (SD) | 75.8 (12.0) | 79.5 (10.6) |

TABLE 11-continued

Secondary efficacy endpoint - Change from baseline in BCVA- mITT population

| Best Corrected Visual Acuity (ETDRS letters score) | Placebo (N = 20) | SAR153191 200 mg q2w (N = 38) |
|---|---|---|
| Median | 79.0 | 80.0 |
| Min:Max | 55:95 | 52:100 |
| Change from | | |
| Number | 15 | 29 |
| Mean (SD) | 3.60 (6.5) | 8.93 (9.9) |
| Median | 4.0 | 7.0 |
| Min:Max | −9.0:20.0 | −5.0:45.0 |
| LS Mean (SE) [a] | 3.5 (1.84) | 9.3 (1.36) |
| 90% CI | (0.32 to 6.59) | (6.97 to 11.61) |
| LS Mean difference (SE) vs. placebo [a] | | 5.8 (2.26) |
| 90% CI | | (1.99 to 9.67) |
| 95% CI | | (1.21 to 10.46) |
| p-value | | 0.0153 |

CI: confidence interval;
MMRM: Mixed model for repeated measurements;
LS mean: least square mean calculated using mixed model
Note:
only patients who had BCVA assessed at baseline and post-baseline are included.
[a] MMRM model with treatment groups, randomization strata of VH level (<4, >=4), visits and visit-by-treatment groups interaction as fixed categorical effects, as well as, fixed continuous covariate of baseline BCVA
An unstructured correlation matrix is used to model the within-patient errors.
Within group LS means and standard errors (SE) are calculated using weights equal to the observed proportion of patients in strata variable levels: VH level (<4, >=4) in the study population BCVA and CRT Preliminary Conclusions At Week 16, patients in the sarilumab group showed a statistically significant improvement in BCVA compared to placebo (LS mean difference vs. placebo of 5.8 (90% CI:1.99-9.67, p=0.0153). The mean reduction in adjudicated CRT (i.e. in macular edema) was numerically higher in the sarilumab group when compared to the placebo group (LS mean difference vs. placebo 5.8 (90% CI: 1.99 to 9.67); p=0.0153).

Anterior Chamber Cells Score

The inflammatory activity in the anterior chamber was qualified through the quantification of cells and proteins in the aqueous humor (Tyndall phenomenon or SUN classification). The percentage of patients with anterior chamber cells score=0 or with at least 2-step reduction was similar for both the sarilumab group and the placebo group, 86.2% and 86.7%, respectively. Results for the sensitivity analysis considering patients with missing data at Week 16 as non-responders were similar to the original analysis.

Percentage of Patients with Prednisone Dose of ≤5 mg/Day (or Equivalent Corticosteroid) at Week 16

The proportion of patients with prednisone dose of ≤5 mg/day (or equivalent corticosteroid) at Week 16 was similar for the sarilumab and placebo group, 41.4% and 40.0%, respectively. Results for the sensitivity analysis considering patients with missing data at Week 16 as non-responders were similar to the original analysis. Mean change from baseline prednisone or oral corticosteroid dose by time windowed visits for the principal treatment period were also analyzed.

Percentage of Patients with a 2-Step Reduction In Vitreous Haze Based on the Miami 7 Point Scale at Week 16

The proportion of patients with 2-step reduction in VH based on the Miami 7-point scale was higher in the sarilumab group (21.4%) when compared with placebo (7.7%), however the difference was not statistically significant (p=0.3164). Results for the sensitivity analysis considering patients with missing data at Week 16 as non-responders were similar to the original analysis.

Exploratory Efficacy Endpoints

At the end of the extension treatment period (Week 52), the percentage of responders (2-step or greater reduction in adjudicated vitreous haze or dose of prednisone <10 mg/day [or equivalent oral corticosteroid]), non-responders, and patients for whom response could not be determined was similar for both treatment groups (Table 12). A 2-step reduction or greater was observed for 7.9% of patients in the sarilumab group compared to none in the placebo group.

Patients who experienced worsening or those defined as non-responders at Week 16 were eligible to continue treatment with sarilumab in the open-label period, part C. Of the 21 patients who entered the open-label phase, 8 (38.1%) had a corticosteroid dose <10 mg/day at Week +36 and were considered to be responders.

TABLE 12

Components of proportion of patients with 2-step or greater reduction in adjudicated VH or a dose of prednisone or equivalent oral corticosteroid < 10 mg/day at Week 52 (end of extension treatment period) - mITT population

| | Placebo (N = 20) | SAR153191 200 mg q2w (N = 38) |
|---|---|---|
| Responders | 6 (30.0%) | 11 (28.9%) |
| Decrease in VH ≥ 2 at Week 52 and corticosteroids dose < 10 mg/day at Week 52 | 0 | 3 (7.9%) |
| Corticosteroids dose < 10 mg/day at Week 52 | 6 (30.0%) | 8 (21.1%) |
| Non-responders | 8 (40.0%) | 16 (42.1%) |
| Did not complete the principal treatment period (part A) due to lack of efficacy | 6 (30.0%) | 6 (15.8%) |
| Did not complete the overall treatment period due to lack of efficacy | 0 | 5 (13.2%) |
| No decrease in VH ≥ 2 and corticosteroids dose >= 10 mg/day at Week 52 | 1 (5.0%) | 1 (2.6%) |
| No decrease in VH ≥ 2 and corticosteroids dose missing at Week 52 | 0 | 2 (5.3%) |
| Non-responder according to medical review | 1 (5.0%) | 2 (5.3%) |
| Responder status cannot be determined | 6 (30.0%) | 11 (28.9%) |
| Complete the principal treatment period (part A) but entered in part C | 5 (25.0%) | 6 (15.8%) |
| Did not complete the principal treatment period (part A) for other reason than lack of efficacy | 1 (5.0%) | 4 (10.5%) |
| Did not complete the overall treatment period for other reason than lack of efficacy | 0 | 1 (2.6%) |

Overall treatment period consists here of the principal + extension treatment period (part A + part B)
Part C is the open-label treatment period.
Analysis is performed using values on time windowed Week 52.

Change from Baseline In Vitreous Haze at Week 52 (Week +36 for Part C)

The difference for the change in adjudicated VH from baseline that was observed at Week 16 was maintained through to Week 52 for patients who entered the extension treatment period. Change in adjudicated VH (according to the Miami 9-step scale) at Week 52 was −1.1 in the sarilumab group and −0.4 for the placebo group.

Patients in the open-label period showed a smaller reduction in VH than those who received sarilumab in the extension. No change in adjudicated VH (according to the Miami 9-step scale) from baseline was observed at Week +36 and the greatest change (−0.4) was observed at Week 28 or subsequent weeks.

Percentage of Patients with Dose of Dose of Prednisone Mg/Day or <10 mg/Day (or Equivalent Oral Corticosteroid) at Week 52 (Week +36 for Part C)

The majority of patients in the treatment extension period had a dose of prednisone mg/day and this was similar for the sarilumab and placebo groups, 85.7% and 87.5%, respectively. In the open-label period, the percentage of patients with a dose of prednisone <10 mg/day was 61.5% and mg/day was 53.8%.

Percentage of Patients with an Anterior Chamber Score=0 or a 2-Step or Greater Reduction in Score at Week 52 (Week +36 for Part C)

At Week 52, the percentage of patients who were responders (anterior chamber score=0 or at least 2-step reduction in score) was smaller for the sarilumab group than for the placebo group. Of the 21 patients who received sarilumab in the open-label period, 12 (57.1%) were responders. Anterior chamber cells score descriptive statistics by time windowed visits were analyzed for the principal and extension period and for the open-label period.

Change from Baseline in Best Corrected Visual Acuity at Week 52 (Week +36 for Part C)

The difference for the change in BCVA from baseline to Week 16 was maintained through to Week 52 for patients who entered the extension treatment period. Data show that the change in BCVA at Week 52 was higher in the sarilumab group compared to the placebo group.

Patients in the open-label period showed improvements in BCVA, change from baseline BCVA was 4.5 ETDRS letters at Week +36 and the greatest change (5.9 ETDRS letters) was observed at Week +28.

Change from Baseline in Central Retinal Thickness (Automatically Generated by the Device, Software from Centralized Spectral Domain Optical Coherence Tomography at Week 52 (Week +36 for Part C)

Improvements in adjudicated CRT that were observed for patients in the sarilumab group at Week 16 were maintained through to Week 52. Mean change from baseline adjudicated CRT at Week 52 was −71.1 µm in the sarilumab group compared to −3.4 µm. However, it should be noted that patients who continued in the study in the extension period were considered responders at the end of the principal treatment period.

Improvements in adjudicated CRT were also observed for patients in the open-label period. Data show that the mean change from baseline adjudicated CRT at Week +36 was −37.5 µm.

Efficacy Data Analysis

At Week 16, the proportion of patients with a 2-step reduction in VH per adjudicated assessment or corticosteroids dose <10 mg/day was higher in the sarilumab group (46.1%) compared with the placebo group (30.0%), however, the difference was not statistically significant (p=0.2354).

At Week 16, the proportion of patients with a 2-step reduction in VH per

Investigator assessment or corticosteroids dose <10 mg/day was higher in the sarilumab group (64.0%) when compared with the placebo group (35.0%; nominal p=0.0372). The other sensitivity analyses using observed case and considering missing responder status as non-responder produced similar results as the primary analysis.

The results of the secondary efficacy endpoints showed statistically significant differences in adjudicated VH, BCVA, adjudicated CRT, and change from baseline CRT at Week 16.

The LS mean change in adjudicated VH from baseline to Week 16 was higher in the sarilumab group (−0.9) compared to the placebo group (−0.1) with an LS mean difference versus placebo of −0.7 (90% CI: −1.223 to −0.262); p=0.0127.

The LS mean change in BCVA from baseline to Week 16 was significantly higher in the sarilumab group (9.3) compared to the placebo group (3.5) with an LS mean difference versus placebo of 5.8 (90% CI: 1.99 to 9.67); p=0.0153.

The LS mean change in adjudicated CRT from baseline to Week 16 was decreased to a greater extent in the sarilumab group (−35.4 µm) when compared to the placebo group (−8.9 µm) with an LS mean difference versus placebo of −26.5 (90% CI: −50.41 to −2.68); p=0.0683.

The LS mean change in adjudicated CRT from baseline to Week 16 was decreased in the sarilumab group (−6.4%) when compared to no change in the placebo group (0.0%) with an LS mean difference versus placebo of −6.4% (90% CI: −12.374 to −0.350); p=0.0825.

Excluding patients with high baseline CRT decreased adjudicated CRT at Week 16 in the sarilumab group and increased adjudicated CRT in the placebo group. These data resulted in an LS mean difference of sarilumab versus placebo of −7.06 (90% CI: −2.022 to 7.904; p=0.4328). Secondary endpoint analyses of anterior chamber cells score and proportion of patients with prednisone dose of mg/day (or equivalent corticosteroid) at Week 16 was not observed to have a statistically significant difference between the sarilumab and placebo treatment groups.

Exploratory endpoint analyses showed that the differences in change in adjudicated VH from baseline, change in BCVA from baseline, and change in CRT from baseline that were observed at Week 16 were maintained at Week 52. Secondary pharmacodynamic analyses showed that levels of both hs-CRP and SAA were decreased from Week 4 in the sarilumab group compared to the placebo group and that the suppression was maintained until Week 52.

Primary and Secondary Analysis of Patients at 52 Weeks

Tables 13-16 below show patient disposition, the underlying etiology of the patients analyzed in this study and baseline disease characteristics.

TABLE 13

Patient Disposition

|  | Placebo | Sarilumab | All Randomized |
|---|---|---|---|
| Randomized and treated | 20 (100%) | 38 (100%) | 58 (100%) |
| Completed Week 16 | 13 (65.0%) | 28 (73.7%) | 41 (70.7%) |
| Completed Week 52 | 7 (35.0%) | 12 (31.6%) | 19 (32.8%) |
| Entered Open Label Rescue | 11 (55.0%) | 10 (26.3%) | 21 (36.2%) |
| Discontinued | 2 (10.0%) | 16 (68.4%) | 18 (31.0%) |
| Adverse event | 1 (5.0%) | 5 (13.2%) | 6 (9.67%) |
| Lack of efficacy | 1 (5.0%) | 7 (18.4%) | 8 (13.8%) |
| Other reasons | 0 | 4 (2.6%) | 4 |

TABLE 14

Baseline Disease Characteristics

|  | Placebo q2 wks (N = 20) | Sarilumab q2 wks (N = 20) | All Randomized (n = 58) |
| --- | --- | --- | --- |
| Recently active disease, n (%) | 1 (5.0%) | 2 (5.3%) | 3 (5.2%) |
| Active disease, n (%) | 19 (95.0%) | 36 (94.7%) | 55 (94.8%) |
| Anatomic location |  |  |  |
| Intermediate | 5 (25.0%) | 7 (18.4%) | 12 (20.7%) |
| Posterior | 2 (10.0%) | 12 (31.6%) | 14 (24.1%) |
| Pan-uveitis | 12 (60.0%) | 17 (44.7%) | 29 (50.0%) |
| Time from first diagnosis |  |  |  |
| Months (SD) | 55.5 (71.9) | 39.1 (58.1) | 44.7 (62.9) |
| Min:Max | 0.6:300.3 | 0.0:286.7 | 0.0:300.3 |

TABLE 15

Disease Characteristics - Underlying Etiology

|  | Placebo q2 wks (N = 20) | Sarilumab q2 wks (N = 20) | All Randomized (n = 58) |
| --- | --- | --- | --- |
| Idiopathic, n (%) | 13 (65%) | 25 (65.8%) | 38 (65.5%) |
| Behcet's | 4 (20%) | 6 (15.8%) | 10 (17.2%) |
| Sarcoidosis | 2 (10%) | 2 (5.3%) | 4 (6.9%) |
| Psoriasis | 0 | 1 (2.5%) | 1 (1.7%) |
| Rheumatoid Arthritis | 0 | 1 (2.6%) | 1 (1.7%) |
| Vogt-Koyangi-Harada | 1 (5.0%) | 1 (2.6%) | 1 (1.7%) |
| Unknown vasculitis | 0 | 2 (5.0%) | 2 (3.4%) |

TABLE 16

Baseline Disease Characteristics

|  | Placebo q2 wks (N = 20) | Sarilumab q2 wks (N = 20) | All Randomized (n = 58) |
| --- | --- | --- | --- |
| Vitreous Haze Investigator |  |  |  |
| Mean (SD) | 2.2 (1.6) | 2.2 (1.9) | 2.2 (1.8) |
| Min:Max | 0:5 | 0:7 | 0:7 |
| VH ≥2, n (%) | 13 (65%) | 21 (55.3%) | 34 (58.6%) |
| Mean (SD) | 3.2 (1.1) | 3.5 (1.5) | 3.2 (1.1) |
| CRT (μm) (Reading Center) |  |  |  |
| Mean (SD) | 306 (58.9) | 338 (155.5) | 327 (130.8) |
| Min:Max | 214:432 | 153:1048 | 153.0:1048 |
| CRT ≥300 μm, n (%) | 11 (55.0%) | 18 (47.4%) | 29 (50.0%) |
| Mean (SD) | 346 (42.3) | 432 (181.5) | 400 (149.7) |
| BCVA (ETDRS Letters) |  |  |  |
| Mean (SD) | 74.5 (13.5) | 70.4 (14.6) | 71.8 (14.2) |
| Min:Max | 35.0:88.0 | 24.0:93.0 | 24.0:93.0 |

Data show that VH, BCVA, and CRT were all improved in patients treated with sarilumab for 16 weeks compared with placebo treated patients. At week 52, the sarilumab group continued to show an advantage over the placebo group; particularly with regard to improvement in CRT in patients with demonstrable macular edema at baseline. The data described herein indicate that sarilumab was effective in increasing BCVA and resolving macular edema in patients with severe uveitis.

The invention claimed is:

1. A method for treating macular edema in a subject in need thereof comprising administering an effective amount of an antibody that specifically binds human IL-6 receptor, wherein the antibody that specifically binds to the IL-6 receptor comprises a heavy chain variable region comprising the sequence of SEQ ID NO: 2 and a light chain variable region comprising the sequence of SEQ ID NO: 3, wherein the antibody is administered every two weeks at a dose of about 150 or about 200 mg and wherein the subject has been treated for at least three months with a corticosteroid.

2. The method of claim 1, wherein the corticosteroid is prednisone.

3. The method of claim 2, wherein the prednisone was administered from 15 to 80 mg/day.

4. A method for treating uveitis in a subject in need thereof comprising administering an effective amount of an antibody that specifically binds IL-6 receptor, wherein the subject has a vitreous haze (VH) level greater than or equal to 2 on the Miami 9 step scale or wherein the subject has a central retinal thickness (CRT) greater than 300 µm, wherein the antibody that specifically binds to the IL-6 receptor comprises a heavy chain variable region comprising the sequence of SEQ ID NO:2 and a light chain variable region comprising the sequence of SEQ ID NO:3, wherein the antibody is administered every two weeks at a dose of about 150 or about 200 mg and wherein the subject has been treated for at least three months with a corticosteroid, wherein at least one symptom of uveitis in the subject is improved, wherein the symptom of uveitis is selected from the group consisting of elevated VH level, reduced best corrected visual acuity (BCVA), macular edema, signs of ocular inflammation, CRT and ocular inflammation in the anterior chamber.

5. The method of claim 4, wherein the corticosteroid is prednisone.

6. The method of claim 5, wherein the prednisone was administered from 15 to 80 mg/day.

7. The method of claim 4, wherein the antibody is sarilumab and the antibody is administered every two weeks at a dose of 150 mg.

8. The method of claim 4, wherein the antibody is sarilumab and the antibody is administered every two weeks at a dose of 200 mg.

9. The method of claim 4, wherein the subject experiences a greater than 20% reduction in CRT,
greater than 10 letters of improvement in best corrected visual acuity (BCVA),
shows a reduction in retinal vessel leakage, and/or
an improvement in uveitis clinical assessment score.

10. A method of treating uveitis in a subject in need thereof comprising administering to the subject a therapeutically effective amount of an antibody, wherein the antibody comprises a heavy chain variable region comprising the sequence of SEQ ID NO:2 and a light chain variable region comprising the sequence of SEQ ID NO:3, wherein the antibody is administered every two weeks at a dose of about 150 or about 200 mg and wherein the subject has been treated for at least three months with a corticosteroid, wherein at least one symptom of uveitis in the subject is improved, wherein the symptom of uveitis is selected from the group consisting of elevated VH level, reduced best corrected visual acuity (BCVA), macular edema, signs of ocular inflammation, CRT and ocular inflammation in the anterior chamber.

11. The method of claim 10, wherein the antibody is sarilumab.

12. The method of claim 10, wherein the uveitis is selected from the group consisting of intermediate uveitis, posterior uveitis and pan-uveitis;
or wherein the uveitis is non-infectious uveitis;
or wherein the uveitis is systemic or idiopathic;
or wherein the subject is suffering from macular edema;
or wherein the subject has a CRT greater than 300 µm.

13. The method of claim 10, wherein the subject has a VH level greater than or equal to 2 on the Miami 9 step scale.

14. The method of claim 10, wherein the subject is suffering from macular edema.

15. The method of claim 10, wherein the subject has other signs of intraocular inflammation selected from the group consisting of perivascular sheathing of retinal vessels and leakage of retinal vessels.

16. The method of claim 10, wherein the corticosteroid is prednisone.

17. The method of claim 16, wherein the prednisone is administered from 15 to 80 mg/day.

18. The method of claim 10, wherein the subject is also administered methotrexate.

19. The method of claim 18, wherein the methotrexate is administered from 6 to 25 mg/week.

20. The method of claim 10, wherein the subject achieves after 16 weeks a reduction in the VH level on the Miami 9 point scale of at least 2 steps or a reduction of corticosteroid dose to less than 10 mg per day.

21. The method of claim 10, wherein the subject achieves after 16 weeks a reduction in VH level on the Miami 9 point scale of at least 2, or a reduction of corticosteroid dose to less than 10 mg per day.

22. The method of claim 10, wherein the subject experiences a greater than 20% reduction in CRT, greater than 10 letters of improvement in best corrected visual acuity (BCVA), shows a reduction in retinal vessel leakage, and/or an improvement in uveitis clinical assessment score.

23. The method of claim 10, wherein the antibody is sarilumab and the antibody is administered every two weeks at a dose of 150 mg.

24. The method of claim 10, wherein the antibody is sarilumab and the antibody is administered every two weeks at a dose of 200 mg.

\* \* \* \* \*

UNITED STATES PATENT AND TRADEMARK OFFICE
CERTIFICATE OF CORRECTION

| | | |
|---|---|---|
| PATENT NO. | : 10,968,278 B2 | Page 1 of 1 |
| APPLICATION NO. | : 15/342833 | |
| DATED | : April 6, 2021 | |
| INVENTOR(S) | : Sundaram et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 544 days.

Signed and Sealed this
Twentieth Day of December, 2022

Katherine Kelly Vidal
*Director of the United States Patent and Trademark Office*